US011793758B2

(12) United States Patent
Rademaker et al.

(10) Patent No.: US 11,793,758 B2
(45) Date of Patent: Oct. 24, 2023

(54) FORMULATIONS OF BIOLOGICAL POLYMERS FOR ORAL ADMINISTRATION

(71) Applicant: Bioralix B.V., Fochteloo (NL)

(72) Inventors: Bernardus Rademaker, Onstwedde (NL); Willem Adriaan Minnaard, Amsterdam (NL); Eduard Johannes Van Zwieten, Purmerend (NL); Jacob Wieling, Fochteloo (NL)

(73) Assignee: Bioralix B.V., Fochteloo (NL)

( * ) Notice: Subject to any disclaimer, the term of this patent is extended or adjusted under 35 U.S.C. 154(b) by 191 days.

(21) Appl. No.: 17/255,376

(22) PCT Filed: Jun. 21, 2019

(86) PCT No.: PCT/NL2019/050384
§ 371 (c)(1),
(2) Date: Dec. 22, 2020

(87) PCT Pub. No.: WO2019/245373
PCT Pub. Date: Dec. 26, 2019

(65) Prior Publication Data
US 2021/0259973 A1    Aug. 26, 2021

(30) Foreign Application Priority Data

Jun. 22, 2018 (EP) .................................... 18179379

(51) Int. Cl.
*A61K 9/14* (2006.01)
*A61K 9/16* (2006.01)
*A61K 9/00* (2006.01)
*C07K 16/42* (2006.01)
*B82Y 5/00* (2011.01)

(52) U.S. Cl.
CPC .......... *A61K 9/1694* (2013.01); *A61K 9/0053* (2013.01); *A61K 9/1652* (2013.01); *C07K 16/4291* (2013.01); *A61K 9/1623* (2013.01); *A61K 9/1658* (2013.01); *B82Y 5/00* (2013.01)

(58) Field of Classification Search
None
See application file for complete search history.

(56) References Cited

U.S. PATENT DOCUMENTS

| 6,576,264 B1* | 6/2003 | Henriksen | B01F 25/281 424/490 |
| 2002/0160109 A1* | 10/2002 | Yeo | B01J 13/046 427/213.3 |
| 2005/0142205 A1* | 6/2005 | Rashba-Step | A61K 9/0019 424/490 |

FOREIGN PATENT DOCUMENTS

| EP | 1093818 A1 | 4/2001 |
| JP | 2015-519343 A | 7/2015 |
| WO | 2005004838 A1 | 1/2005 |
| WO | 2013/177198 A1 | 11/2013 |

OTHER PUBLICATIONS

International Search Report for International Application No. PCT/NL2019/050384, dated Sep. 3, 2019, 4 pages.
International Search Report for International Application No. PCT/NL2019/050384, dated Sep. 3, 2019, 6 pages.
Okamoto et al, "Stability of chitosan-pDNA complex powder prepared by supercritical carbon dioxide process", Feb. 16, 2005 (Feb. 16, 2005), vol. 290, No. 1-2, p. 73-81, XP027623867.
Japanese Notice of Reasons for Refusal for Japanese Application No. 2021-520902, dated May 18, 2023, 7 pages (English translation).

* cited by examiner

*Primary Examiner* — Susan T Tran
(74) *Attorney, Agent, or Firm* — TraskBritt

(57) ABSTRACT

The disclosure relates, among others, to methods for preparing pharmaceutical compositions that can be provided to the subject in oral form, comprising as an active ingredient: a protein with a mass of 10 kilodalton or more, a nucleic acid molecule of 15 nucleotides or more, or a combination thereof. The one or more active ingredients are distributed in particles in a way that facilitates the uptake of the particles by the intestine and the release of the active ingredient(s) into the blood stream. Methods for preparing such pharmaceutical compositions comprise preparing an aqueous composition comprising one or more active ingredients; a mono- or disaccharide; one or more further compounds and chitosan; and spraying the prepared aqueous composition into an anti-solvent and/or supercritical fluid in which the water fraction of the composition is soluble or miscible and in which the solutes of the composition are not soluble, thereby precipitating the solutes and producing particles with an average diameter of 50 nanometers (nm) to 20 micrometers (um); collecting the particles; and preparing the pharmaceutical composition comprising the particles. Also provided are collections of particles with an average diameter of 50 nm to 20 um comprising a homogeneous distribution of indicated ingredients. Also provided is a pharmaceutical formulation in oral dosage form comprising such a collection of particles for use in the treatment of a disease.

19 Claims, 21 Drawing Sheets

| Sample | Weight average sedimentation coefficient (S) | Proportion of total signal (%) | Frictional ratio |
|---|---|---|---|
| 1 | 3.7 | 2.5 | 1.88 |
|   | 5.7 | 97.5 |  |
| 2 | 6.3 | 61.1 | 1.5 |
|   | 9.7 | 16.6 |  |
|   | 15.2 | 15.7 |  |

Continuous sedimentation coefficient distribution for sample 1 (left) and 2 (right)

FORMULATIONS OF BIOLOGICAL POLYMERS FOR ORAL ADMINISTRATION

CROSS-REFERENCE TO RELATED APPLICATIONS

This application is a national phase entry under 35 U.S.C. § 371 of International Patent Application PCT/NL2019/050384, filed Jun. 21, 2019, designating the United States of America and published as International Patent Publication WO 2019/245373 A1 on Dec. 26, 2019, which claims the benefit under Article 8 of the Patent Cooperation Treaty to European Patent Application Serial No. 18179379.5, filed Jun. 22, 2018.

TECHNICAL FIELD

The disclosure relates to pharmaceutical formulations for gastro-intestinal delivery of biological polymers such as protein and nucleic acid molecules. The disclosure also relates to method for producing such formulations.

BACKGROUND

The uptake of particles, containing biological macromolecules, via the gastrointestinal system and delivered via the oral route, is hampered through a series of barriers, e.g., a low regional pH, digestive enzymes and the presence of mucus layers preventing passive uptake (Lundquist P., Artusson P. *Adv Drug Del Rev* 106: 256-276, 2016 and Muheem A., et al., *Saudi Pharm J* 24(4): 379-506, 2016).

The digestive tract contains several systems that facilitate the uptake of biological molecules. Most of these systems are specific for particular substances. Recently it has been shown that also particles can cross the intestinal barrier. The exact route that is taken by particles is not known and may differ depending on the type of particle. Some studies suggest that some particles migrate via M-cells and so-called Peyer's Patches.

Methods to pass the harsh environment of the stomach are readily available. Such methods include but are not limited to enteric coating of tablets or pill, delayed release formulations and capsules that are resistant to acidic environments. Such delivery vehicle preferably comprises the particles, which are released after passage of the stomach. Such stomach passing delivery vehicles deliver the particles essentially intact to the environment after the stomach. This is preferably the small intestine and/or the colon. The trigger for facilitating release in the small intestine can favorably be the pH, time to allow degradation of the vehicle after a certain time has passed, such as in slow or delayed release formula's and/or the presence of digestive enzymes. The trigger for facilitating release in the colon can favorably be time, for instance, in delayed or slow release formulas. Delayed release formula's typically release their content in immediately after the passage of a certain amount of time. Slow release formula's typically release continuously over a longer period of time, release can be triggered at a certain time point, or change of environment or other signal, release can, but does not have to be constant over the period of time. After protection to the gastric low pH, the remaining digestive tract contains systems like absorptive enterocytes in the microvilli. Passive and active transport mechanisms over the intestinal wall can be targeted for particle uptake. Loading of the particles with a biological molecule can facilitate release of the biological molecule from the particles into the blood stream.

The oral delivery of biologically active macromolecules (biologics) has been a challenge thus far and moderately successful for small biologics only. Millotti et al. (2011) describe the preparation of chitosan-6-mercaptonicotinic acid particles for the oral delivery of human insulin. Insulin with a molecular size of <6 kDa does by itself not pass the intestinal wall but does so with a low bioavailability when associated to thiolated chitosan comprising particles (Millotti et al., 2011 *Drug Delivery* 18(3) 190-197).

Proteins having a kDa ranging from 10-500 kDa and oligonucleotides are currently delivered by intravenous or subcutaneous injection only. The low bioavailability (<10%) of peptides and proteins in oral formulations, initiated extensive research into better means and methods. Such research involved, among others the use of permeation enhancers with mixed results (see Whitehead K., et al., *Pharm Res* 25 (8): 1782-1788, 2007; Yewale C., et al., *Clin Rev Therap Drug Carrier Systems* 32 (5): 236-387, 2015). These methods have yet to evolve into common practice.

The disclosure provides particles and methods of making the particles with which it is possible to effectively cross the intestinal barrier and once in the bloodstream effectively make a trapped protein or nucleic acid molecule bioavailable.

BRIEF SUMMARY

The disclosure provides a method for preparing a pharmaceutical composition comprising as an active ingredient: a protein with a mass of 10 kilo Dalton or more, a nucleic acid molecule of 15 nucleotides or more, or a combination thereof, comprising preparing an aqueous composition that comprises one or more active ingredients; a mono- or disaccharide; one or more further compounds and chitosan; and spraying the prepared aqueous composition into an anti-solvent and/or supercritical fluid in which the water fraction of the composition is soluble or miscible and in which the solutes of the composition are not soluble, thereby precipitating the solutes and producing particles with an average diameter of 50 nanometers (nm) to 20 micrometers (um); collecting the particles; and preparing the pharmaceutical composition comprising the particles. Also provided are collections of particles with an average diameter of 50 nm to 20 um comprising a homogeneous distribution of indicated ingredients. The indicated ingredients are specified in the claims and comprise the active ingredient (a protein with a mass of 10 kiloDalton or more, a nucleic acid molecule of 15 nucleotides or more), the chitosan and the other indicated ingredients. Also provided is a pharmaceutical formulation in oral dosage form comprising such a collection of particles for use in the treatment of a disease.

In one embodiment is provided a method for preparing a pharmaceutical composition comprising:
  preparing an aqueous composition comprising:
    a protein with a mass of 10 kiloDalton or more, a nucleic acid molecule of 15 nucleotides or more, or a combination thereof, as an active ingredient in an amount of 0.02-25% of the dry weight of the composition;
    mono- or disaccharide in an amount of 2-25% of the dry weight of the composition;
    one or more further compounds in an amount of 0-10% of the dry weight of the composition;
    chitosan in an amount of at least 48.3% of the dry weight of the composition;
  spraying the prepared aqueous composition into an anti-solvent and/or supercritical fluid in which the water fraction of the composition is soluble or miscible and in which the solutes of the composition are not soluble, thereby precipitating the solutes and producing particles with an average diameter of 50 nanometers (nm) to 20 micrometers (um);

collecting the particles; and preparing the pharmaceutical composition comprising the particles.

Also provided is a method for preparing a pharmaceutical composition for oral delivery of an systemically active ingredient comprising:

preparing an aqueous composition comprising
a protein with a mass of 10 kilodalton or more, a nucleic acid molecule of 15 nucleotides or more, or a combination thereof, as a systemically active ingredient in an amount of 0.02-25% of the dry weight of the composition;
mono- or disaccharide in an amount of 2-25% of the dry weight of the composition;
one or more further compounds in an amount of 0-10% of the dry weight of the composition;
chitosan in an amount of at least 48.3% of the dry weight of the composition;
spraying the prepared aqueous composition into an antisolvent and/or supercritical fluid in which the water fraction of the composition is soluble or miscible and in which the solutes of the composition are not soluble, thereby precipitating the solutes and producing particles with an average diameter of 50 nanometers (nm) to 20 micrometers (um);
collecting the particles; and preparing the pharmaceutical composition for oral delivery comprising the particles comprising the systemically active ingredient.

The prepared aqueous composition preferably comprises one or more further compounds in an amount of 0-8%, preferably 0-6%, preferably 0-4%, preferably 0-2%, preferably 0-1.7% of the dry weight of the composition.

In one embodiment the disclosure provides a method for preparing a pharmaceutical composition comprising:

preparing an aqueous composition comprising
a protein with a mass of 10 kilodalton or more, a nucleic acid molecule of 15 nucleotides or more, or a combination thereof, as an active ingredient in an amount of 0.02-25% of the dry weight of the composition;
mono- or disaccharide in an amount of 2-25% of the dry weight of the composition;
one or more further compounds in an amount of 0-1.7% of the dry weight of the composition;
chitosan in an amount of at least 48.3% of the dry weight of the composition;
spraying the prepared aqueous composition into an antisolvent and/or supercritical fluid in which the water fraction of the composition is soluble or miscible and in which the solutes of the composition are not soluble, thereby precipitating the solutes and producing particles with an average diameter of 50 nanometers (nm) to 20 micrometers (um);
collecting the particles; and preparing the pharmaceutical composition comprising the particles.

The disclosure provides a method for preparing a pharmaceutical composition comprising:

preparing an aqueous composition comprising
as an active ingredient: a protein with a mass of 10 kilodalton or more, a nucleic acid molecule of 15 nucleotides or more, or a combination thereof, in an amount of 0.001-1.5% by weight of the final aqueous composition;
a mono- or disaccharide in an amount of 0.1-1.5% by weight of the final aqueous composition;
one or more further compounds in an amount of 0.0-0.5 preferably 0.1% by weight of the final aqueous composition;
chitosan in an amount of at least 0.5% by weight of the final aqueous composition;
spraying the prepared aqueous composition into an antisolvent in which the water fraction of the composition is soluble or miscible and in which the solutes of the composition are not soluble;
precipitating the solutes thereby producing particles with an average diameter of 50 nanometers (nm) to 20 micrometers (um);
collecting the particles; and
preparing the pharmaceutical composition comprising the particles.

The aqueous composition prepared preferably comprises one or more further compounds in an amount of 0.0-0.4% by weight of the final aqueous composition, preferably 0.0-0.3%, preferably 0.0-0.2%, and preferably 0.0-0.1% by weight of the final aqueous composition.

The disclosure further provides a collection of particles with an average diameter of 50 nm to 20 um obtainable by a method as described herein.

A method for preparing a pharmaceutical composition as described herein preferably further comprises preparing an oral dosage form comprising prepared particle or collection of particles.

The prepared pharmaceutical composition is preferably a pharmaceutical composition for oral delivery of a systemically active ingredient.

Also provided is a collection of particles with an average diameter of 50 nm to 20 um comprising a homogeneous distribution of
a protein with a mass of 10 kilodalton or more, a nucleic acid molecule of 15 nucleotides or more, or a combination thereof, as an active ingredient in an amount of 0.02-25% of the dry weight of the particles;
mono- or disaccharide in an amount of 2-25% of the dry weight of the particles;
one or more further compounds in an amount of 0.0-10, preferably 0.0-8, preferably 0.0-6, preferably 0.0-4, preferably 0.0-2, preferably 1.7% of the dry weight of the particles;
chitosan in an amount of at least 48.3% of the dry weight of the particles.

Further provided is a method for delivering a protein of 10 kDa or more, or a nucleic acid molecule of 15 nucleotides or more, or a combination thereof as an active ingredient in a therapeutically relevant amount to the blood of a subject in need thereof, the method comprising preparing a pharmaceutical composition according to the method as described herein, comprising the protein or the nucleic acid molecule, and orally administering the pharmaceutical composition to the subject.

Also provided is a pharmaceutical formulation in oral dosage form comprising a collection of particles as described herein for use in the treatment of a disease. The formulation is preferably a solid dosage form.

Further provided is a collection of particles as described herein, comprising preferably an antibody as the protein with a molecular mass of 10 kilodalton A method for delivering a protein of 10 kDa or more, or a nucleic acid molecule of 15 nucleotides or more as an active ingredient in a therapeutically relevant amount to the blood of a subject in need thereof, the method comprising preparing a pharmaceutical composition according to the method of any one of claims 1-8, comprising the protein or the nucleic acid molecule, and orally administering the pharmaceutical composition to the subject.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
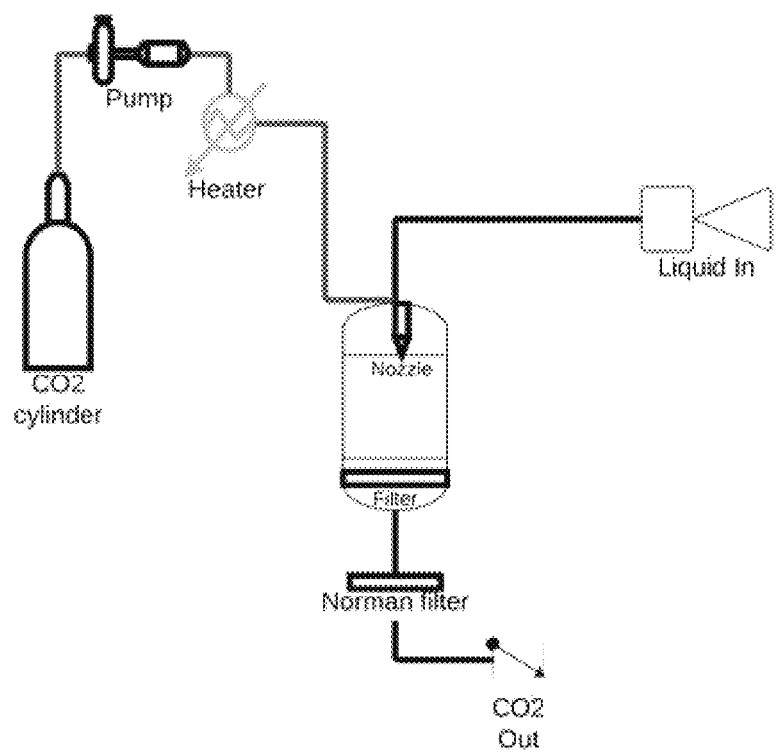
FIG. 1 Schematic overview of an example of a supercritical setup

An "active ingredient" is an ingredient that has a biological effect when provided to a permissive biological system. It is typically an ingredient of which a therapeutic effect is expected upon administration to an individual in need thereof. It can have a therapeutic effect on its own or in combination with one or more other molecules and/or cells. The other molecule(s) and/or cells may be present in the same pharmaceutical composition or in a different one, or already be present in the individual.

The active ingredient is one that has a biological effect when administered or provided to the circulation of an individual. Such ingredients are also referred to as systemically active ingredients. Without being bound by theory it is believed that the inventive particles, collections of particles, compositions and pharmaceutical compositions and other means comprising the particles described herein, are able to pack ingredients, provide stability in the gastro-intestinal tract to the ingredients and facilitate transport of the ingredients from the gastro-intestinal tract to the bloodstream. It is further believed that the particles facilitate slow release of the packed ingredient(s) in the blood of the subject. This leads to an extended bioavailability when compared to i.v. injection of the ingredient, in particular, with proteins of a molecular weight of about 100-300 kDa, such as antibodies. Active ingredients may also be referred to as medicaments.

An active ingredient used in the disclosure is preferably soluble in water. The term "soluble in water" or "water-soluble" means that the water-solubility of the active ingredient is generally not less than about 1 g, preferably not less than about 3 g, more preferably not less than about 5 g, per 100 ml of water at 20° C. Preferably, an active ingredient is readily soluble in water. The term "readily soluble in water" means that the water-solubility of the physiologically active substance is not less than about 5 g, preferably not less than about 10 g, per 100 ml of water at 20° C.

An active ingredient may be a chemical compound or a biological molecule. An active ingredient is preferably a protein with a mass of 10 kiloDalton or more, a nucleic acid molecule of 15 nucleotides or more, or a combination thereof. The pharmaceutical composition may comprise one, two, three or even more active ingredients. The total amount of all the active ingredients with a mass of 10 kiloDalton or more in case of proteins, with 15 nucleotides or more in case of nucleic acid molecules, or a combination thereof together is 0.001-1.5% by weight of the aqueous composition, preferably 0.01-1.5%; more preferably 0.05-1.5%; more preferably 0.1-0.5% by weight of the aqueous composition. Active ingredients that are not proteins or nucleic acid molecules of the indicated mass or number of nucleotides in length can be present in the particles, in which case the weight thereof with respect to the final weight of the aqueous composition is given under "the one or more further compounds." The upper limit of the amount of active ingredient in the aqueous composition can be 1.5%.

An active ingredient is preferably a protein composed of 60 more amino acid residues. The protein includes proteins synthesized by the machinery of a cell, post translationally modified proteins, polypeptides, derivatives thereof. An active ingredient can be a compound having a peptide-like structure. The protein preferably has a molecular weight of about 10 kiloDalton or more, preferably 15 kiloDalton or more, more preferably 20, 30, 50, 75, 100, 125 or 150 kiloDalton or more. In a preferred embodiment the protein has a molecular weight of 100 to 20,000 kiloDalton. The disclosure is particularly useful for proteins of a molecular weight of more than 100 kilodalton. In some embodiments the protein is an antibody. Antibodies have a mass that is typically between 100-300 kiloDalton. The protein is therefore preferably has a molecular weight of 100-300 kiloDalton, preferably approximately 100-200 kiloDalton. The disclosure is particularly suited for proteins or nucleic acid molecules that need to administered repeatedly over a longer period of time. Many proteins and nucleic acid molecules are administered in a more or less invasive way through a needle. Often this requires that the medicament is administered by a qualified person typically in a hospital. A pharmaceutical composition of the disclosure can be administered orally. A pharmaceutical composition of the disclosure facilitates the transfer of a significant amount of active ingredient from the intestinal lumen to the blood stream that transports nutrients from the gastrointestinal tract to the rest of the body. Most but not all of the blood from the gastrointestinal tract passes the liver prior to distribution to the rest of the body. Typically 20% or more of the active ingredient is transferred. In a preferred embodiment at least 30%, preferably at least 40%, more preferably at least 50%, 60%, 70% is transferred to the blood stream.

The terms "mass," "molecular mass" or "molecular weight," "size" or "molecular size" are used inter-changeably in relation to a protein that is in a particle as described herein, and/or in relation to an active ingredient as described herein. As an example, the mass of an antibody, or the molecular mass of an antibody or the molecular weight of an antibody is typically between 100-300 kiloDalton.

The disaccharide is preferably a disaccharide that is biocompatible and biodegradable. Disaccharides have two monosaccharides linked via a glycosidic bonds. Non-limiting examples are lactose, sucrose, cellibiose, trehalose and maltose. In a preferred embodiment at least one of the monosaccharides is glucose. In a preferred embodiment the glycosidic bond is a glucosidic bond. In a preferred embodiment the disaccharide has the chemical formula $C_{12}H_{22}O_{11}$. In a particularly preferred embodiment the disaccharide is sucrose.

The mono- or disaccharide is preferably present in an amount of 0.01-1.5% by weight of the final aqueous composition. Preferably in an amount of 0.01-0.25% by weight of the final aqueous composition. The mono- or disaccharide is preferably present in an amount of 0.1-1.5% by weight of the final aqueous composition. Preferably in an amount of 0.1-0.25% by weight of the final aqueous composition. The upper limit of the amount of mono- or disaccharide in the aqueous composition can be 2%.

Chitosan is a linear polysaccharide composed of randomly distributed β-(1>4)-linked D-glucosamine (deacetylated unit) and N-acetyl-D-glucosamine (acetylated unit). It can be produced by deacetylation of chitin, which is the structural element in the exoskeleton of crustaceans (such as crabs and shrimp) and cell walls of fungi. The degree of deacetylation (% DD) can be determined by NMR spectroscopy. The degree of % DD in a chitosan of the disclosure ranges from 60 to 100%. On average, the molecular weight of a chitosan of the disclosure is between 3800 and 20,000 Daltons. Methods to produce chitosan are known in the art. A common method for the synthesis of chitosan is the deacetylation of chitin using sodium hydroxide in excess as a reagent and water as a solvent. Nowadays, chitosan can also be synthesized chemically. Chitosan as used in the disclosure is typically a weak base and is insoluble in water and organic solvent. However, it is soluble in dilute aqueous acidic solution (pH<6.5), which can convert glucosamine units into soluble form R—NH 3+(Kumar, Muzzarelli, Muzzarelli, Sashiwa, & Domb, 2004). Chitosan as used in the disclosure dissolves in water at an amount of less than 10 mg/ml, preferably less than 5 mg/ml at room temperature and atmospheric pressure.

Chitosan is preferably present in an amount of at least 1% by weight of the final aqueous composition, preferably 2%, preferably 4% more preferably 8%, more preferably at least 16% by weight of the final aqueous composition. Chitosan is preferably present in an amount of 1-10% by weight of the final aqueous composition.

Particles are produced by spraying the aqueous composition into an anti-solvent and/or by spraying the aqueous composition into a supercritical fluid. In a preferably embodiment the prepared aqueous composition is sprayed into an anti-solvent in which the water fraction of the composition is soluble or miscible and in which the solutes of the composition are not soluble. The water fraction of the composition can dissolve in the anti-solvent and/or supercritical fluid. The solvents and/or droplets or particles in the aqueous composition are typically essentially not soluble in the anti-solvent and/or supercritical fluid. Droplets can be present in the context of an emulsion, a colloid and/or a dispersion. Of course, it is conceivable that the aqueous solution comprises a solute, particle or droplet that is quickly soluble in the anti-solvent and/or supercritical fluid. In such a case the solute, particle or droplet typically does not contribute significantly to the particles that are formed in the anti-solvent and/or supercritical fluid. In a preferred embodiment the anti-solvent is a supercritical fluid.

The particles that are produced by a method of the disclosure preferably have an average diameter of 50 nm to 20 um, preferably 50 nm to 10 um, preferably 50 nm to 5 um, preferably 50 nm to 1 um. The most commonly used metrics when describing particle diameter distributions is with a D-Value. D-Values such as D10, D50 & D90 are the intercepts for 10%, 50% and 90% of the cumulative mass. A typical example of the particles produced:

D10 (nm) D50 (nm) D90 (nm)
104 285 854

The D10 value marks the diameter at which the particles with a smaller diameter collectively have a mass that is 10% of the total mass of all the particles in the collection. Similarly, the D50 value marks the diameter at which the particles with a smaller diameter collectively have a mass that is 50% of the total mass of all the particles in the collection. D50 value of the collection of particles and the diameter distribution can be influenced by the following spray variables:

Temperature, nozzle size and shape, pressure, flow rate CO2, flow rate solution, composition of the fluid to be sprayed.

Where herein reference is made to an average diameter of particles the reference is to the D50 value of the collection. In a preferred embodiment the particles have an average diameter of 50-500 nm.

WO2005/004838 describes formulations for intranasal delivery of protein comprising chitosan derivatives. The formulations comprise a blend of protein particles and soluble chitosan. Soluble chitosan is a derivative of chitosan that dissolves in water at an amount of at least 10 mg/ml at room temperature and atmospheric pressure. The formulations do not comprise particles with a homogeneous distribution of at least the protein and the chitosan. Kashid et al. state that particle size and morphology of drug particles constitute important properties for particulate nasal drug products. Particle size and morphology are related to the drug dissolution and should be controlled to obtain suitable drug dissolution properties in the nostrils. In vitro dissolution rates in suitable simulated fluid(s) should be considered. Particle size and morphology are also important to minimize the feel of grittiness and possibly irritation to the nasal cavity. Too fine particles, below five microns may be inhaled into the lungs and should be avoided for nasal products. Generally, particles in the 5-10 micron range are deposited in the nostrils (Kashid et al. (2016). *World Journal of Pharmaceutical Research*. 5. 891-912. DOI10.20959/wjpr20166-6427.

The supercritical fluid preferably has a temperature of 30-55 degrees Celsius. Examples of suitable supercritical fluids are ethane, propane, nitrous oxide ($N_2O$) or carbon dioxide (CO2). The supercritical fluid is preferably supercritical CO2. The pressure of the supercritical fluid is of course high enough to warrant the supercritical state of the supercritical fluid. For CO2 the pressure is preferably at least 73 Bar. Preferably, the pressure is at least 100 Bar, more preferably the pressure is 100-180 Bar.

Flow rates of the CO2 and the aqueous composition are amongst the typical parameters that are known to the skilled person to be adjustable to fine tune the system. Suitable rates are 150-350 kg/hr for CO2 and 2-8 ml/min for the aqueous composition. Similarly the skilled person knows that the size and the shape of the nozzle through which the aqueous composition is sprayed can be varied as desired.

The one or more further compounds can be typical pharmaceutical excipients such as but not limited to one or more amino acids, anti-adherents, binders, coatings, colors, disintegrants, flavors, glidants, lubricants, preservatives, sorbents, sweeteners, etc., or a combination thereof. The one or more further compounds can also encompass an active ingredient that is not a protein with a mass of 10 kilodalton or more, or a nucleic acid molecule of 15 nucleotides or more, or a combination thereof.

The one or more further compounds can be present in an amount of 0-10% by weight of the final aqueous composition, preferably 0.000-0.5%, more preferably 0.005-0.5%, preferably 0.05-0.5% preferably 0.0-0.1%, preferably 0.005-0.1%, preferably 0.01-0.1%, preferably 0.05-0.1%, by weight of the final aqueous composition.

In one embodiment the prepared aqueous composition comprises an amino acid in an amount of 0.005-0.015% by weight of the final aqueous composition, the lower limit of the range is preferably 0.005 more preferably 0.01. The upper limit is preferably 0.015, more preferably 0.01. Any lower range limit can be combined with any higher range limit. The range is preferably 0.001-0.5, more preferably 0.01-0.25, and more preferably 0.02-0.1% by weight of the final aqueous composition.

The amino acid is preferably a histidine, a lysine, an arginine, an asparagine, or a glutamine. The amino acid is preferably a histidine, a lysine or an arginine. Preferably, the amino acid is histidine. When two or more amino acids are present, at least one of them is a histidine, a lysine, an arginine, an asparagine, or a glutamine. In a preferred embodiment, two or more of them are selected from the group consisting of histidine, lysine, arginine, asparagine, and glutamine. Preferably, at least one of them is histidine.

The prepared aqueous composition preferably comprises one or more of a permeation enhancer, a solubilizer; an emulsifier or a combination thereof. Based on their safety profile and effectiveness, permeation enhancing chemicals being, but not limited to, a zwitterionic surfactant, or having a nitrogen-containing ring, or being an anionic surfactant are the preferred addition to the treatment with nanoparticles containing macromolecules.

The solubility in water of poorly water soluble drugs can be enhanced through the action of a solubilizer. The solubilizer can increase the bioavailability of the active ingredient. A well-known solubilizer is cyclodextrin. The aqueous composition may comprise polysorbate 20 to 80 and/or sorbitan stearate.

The content of water in the final aqueous composition can vary. The artisan can use more concentrated or more diluted compositions as desired. The ratio of dry weight to water can be 1-20; 1-30; 1-40; 1-50; 1-60; 1-70; 1-80; 1-90; 1-100; 1-120; 1-140; 1-160; 1-180; 1-200 or lower. In a preferred embodiment the ratio of dry weight to water in the final aqueous composition ranges from rounded 1-25 to 1-200; preferably 1-30 to 1-160; preferably 1-50 to 1-100; preferably 1:27 to 1:166.

The active ingredient may comprise an oligonucleotide, a cytokine, an enzyme, a soluble protein ligand to a cellular receptor, a factor of the blood clotting system, a fusion protein and/or an antibody. In the case of two or more active ingredients, all ingredients may be oligonucleotide, protein or a combination thereof. Combinations of active ingredients are in principle not restricted.

The nucleic acid molecule is preferably an oligonucleotide. The oligonucleotide can be double stranded or single stranded. The oligonucleotide is preferably single stranded. In one embodiment the oligonucleotide is an antisense oligonucleotide. Oligonucleotides are presently being pursued for reasons of manipulation of the level of certain transcripts in a cell. They are also used as guide for Crispr/Cas type genome editing approaches. They are also used as replicating and non-replicating gene expression cassettes, such as but not limited to nucleic acid vaccines, gene therapy vehicles and the like. In the case of two or more active ingredients, it is preferred to have two or more oligonucleotides, preferably two or more oligonucleotides or 15 nucleotides or more. The two or more oligonucleotides can be against different targets, the same target at different positions of the target or a combination thereof. The number of 15 or more nucleotides in a nucleic acid molecule as referred to herein, refers to the length of the nucleic acid molecule. For instance, a double stranded oligonucleotide with two complementary single stranded oligonucleotides of 15 nucleotides each, hybridized to each other is said to be a nucleic acid molecule or an oligonucleotide of 15 nucleotides in length. The nucleic acid molecule is preferably 15-10.000 nucleotides in length, preferably 15-5.000, more preferably 15-2.000 nucleotides in length. An oligonucleotide is preferably of a length that can be synthesized in vitro. Typically such oligonucleotides have a length of 15-60 nucleotides, more preferably 15-40, more preferably 15-25 nucleotides in length. In a preferred embodiment the oligonucleotide is single stranded. The oligonucleotide can on occasion be smaller than 15 nucleotides. Oligonucleotides can have an artificial backbone. Such artificial backbones include but are not limited to locked nucleic acid (LNA); 2'-O-[2-(N-methylcarbamoyl)ethyl]uridine (MCE); 2'-O-methoxyethyl (MOE); 2'-O-methyl (OMe); morpholino; peptide nucleic acids (PNA); phosphorothioate (PS), or combinations thereof.

Cytokines are a broad category of proteins that are important in cell signaling. Their release has an effect on the behavior of cells around them. It can be said that cytokines are involved in autocrine signaling, paracrine signaling and endocrine signaling as immunomodulating agents. Cytokines may include chemokines, interferons, interleukins, lymphokines, and tumor necrosis factors.

Enzymes are proteinaceous catalysts. Enzymes accelerate chemical reactions. The molecules upon which enzymes may act are called substrates and the enzyme converts the substrates into different molecules known as products.

Almost all metabolic processes in the cell need enzyme catalysis in order to occur at rates fast enough to sustain life. Various enzymes are the subject of so-called enzyme replacement therapies. Replacement therapy aims to replace an enzyme that is deficient or absent in the body. Nowadays this is done by giving the patient an intravenous (IV) infusion of a solution containing the enzyme, or a subcutaneous injection with a depot of the enzyme shielded from the native immune system. Replacement therapy is available for some lysosomal storage diseases: Gaucher disease, Fabry disease, MPS I, MPS II (Hunter syndrome), MPS VI and Pompe disease. Adenosine deaminase and prolidase are other non-limiting examples of enzyme replacement therapy. With the particles of the disclosure it is now possible to administer the enzyme orally.

Many cells are receptive to molecules that attach to a cellular receptor. Such molecules can be steroids and other small molecules. Often such receptors are the receptors for a proteinaceous ligand of 10 kDa or more. The proteinaceous molecule is typically a signaling protein. Such a signaling protein can be a growth factor such as but not limited to EGF, a WNT protein such as but not limited to WNT3, a bone morphogenic protein. Proteinaceous ligands can be soluble or be made soluble. For instance, in the case of cell membrane associated proteins, by replacing the transmembrane region and cytoplasmic region (if any) by an Fc tail.

The active ingredient can be a factor of the blood clotting system. The blood clotting system (coagulation) involves both a cellular (platelet) and a protein (coagulation factor) component. Coagulation is induced by a cascade of proteins that interact and stimulate coagulation. This is called the coagulation cascade. It comprises a tissue factor pathway (the so-called extrinsic pathway), a contact activation pathway (the intrinsic pathway) and a common pathway. Various factors have been identified. They are referred to by various names. Often they are simply referred to by number, i.e., factor I-XIII. Other factors are, for example, von Willebrand factor, fibronectin, antithrombin III, protein C, protein S, protein Z, plasminogen etc.

The active ingredient can be a fusion protein. The fusion protein can be made to solubilize an extracellular part of a membrane protein. It can also be a fusion for other reasons.

In a preferred embodiment the active ingredient is an antibody. Antibodies are very useful in many situations. One of the drawbacks of antibodies is that they typically have to be administered over a period of time during a day and have to be administered through a needle in the form of an IV injection, a drip solution, an intramuscular injection or the like. One of the advantages of embodiments of the disclosure is that larger proteins such as antibodies (where IgG have a typical average size of 120-180 kDa depending on additions such as toxins, labels, further binding units and the like) can now be taken up efficiently in an essentially unmodified form upon oral administration. The antibody can be of any isotype. It is preferably an IgG, and IgA, an IgM or a combination thereof. It can be a monoclonal antibody. It can be a bispecific antibody. Various other modalities are also produced nowadays such as a tri-specific, or more specific antibody.

In a preferred embodiment the method comprises providing two or more active ingredients. In this embodiment it is preferred that the active ingredients comprise two or more different antibodies. The antibodies can be directed toward different epitopes on one and the same target molecule. Typically they are directed toward different epitopes one different target molecules. One or more anti-cancer antibodies are preferred. Other preferred antibodies are antibodies against pathogens in the context of a vaccine, or antibodies against one or more pro-inflammatory cytokines in the context of, for instance, auto-immune disease, or antibodies in the treatment of urticaria, allergy, asthma and allergic asthma.

In another preferred embodiment the active ingredient is an antigen binding part of an antibody, or a derivative or an analogue thereof. A suitable part is a FAB fragment, a single chain Fv fragment and other modalities. Nanobodies and monobodies can be used, camelid antibodies such as single heavy chain antibodies can be used. Binding peptides can be used. Suitable peptides are, for instance, the so-called bicycles that are essentially conformational restricted peptides. Derivatives and analogues of parts of antibodies are peptides with the same general structure such as the immunoglobulin fold, but different amino acid sequence. An analogue is a protein with a different structure but similar binding property as an antibody such as a soluble T-cell receptor.

The antibody or part, derivative and/or analogue thereof can also be drug conjugate. Non-limiting examples of such drug-conjugates are antibody drug conjugates (ADC), nanobody drug conjugates (NDC), single chain Fv drug conjugates.

In a preferred embodiment the active ingredient is an interferon, an erythropoietin, an antibody, a Factor VIII, a Factor IX, a Von Willebrand factor, a tumor necrosis factor (TNF), a growth hormone (GH), etanercept, or a prolidase. In a particularly preferred embodiment the antibody is omalizumab.

The disclosure further provides a collection of particles with an average diameter of 50 nm to 20 um obtainable by a method of the disclosure, Also provided is a collection of particles with an average diameter of 50 nm to 20 um comprising a homogeneous distribution of
- a protein with a mass of 10 kilodalton or more, a nucleic acid molecule of 15 nucleotides or more, or a combination thereof, as an active ingredient in an amount of 0.02-25% of the dry weight of the particles;
- mono- or disaccharide in an amount of 2-25% of the dry weight of the particles;
- one or more further compounds in an amount of 0-10%, preferably 0-8%, preferably 0-6%, preferably 0-4%, preferably 0-2%, preferably 0.0-1.7% of the dry weight of the particles
- chitosan in an amount of at least 48.3% and preferably at least 50% of the dry weight of the particles.

The active ingredient, the mono- or disaccharide, the one or more further compounds, the chitosan are the same as described for the method of producing the particles. In one preferred embodiment the active ingredient of the particle is an antibody, preferably the antibody omalizumab.

In a collection of particles as described herein an active ingredient is preferably present in an amount of 0.02-25% of the dry weight of the particles. Preferably the active ingredient is present in an amount of 0.2-20% of the dry weight of the particles, preferably 0.4-15% of the dry weight of the particles, preferably 1.0-10% of the dry weight of the particles. When more than one active ingredient is present the indicated ranges are for all active ingredients together. Mono- or disaccharide is preferably present in an amount of 2-25%, preferably 1-15%, preferably 1-12% of the dry weight of the particles, preferably 2-10%, more preferably 3-8%, preferably 4-6% of the dry weight of the particles. A preferred lower limit of the mono- or disaccharide in these ranges is 2%. The one or more further compounds are preferably present in an amount of 0-12%, preferably 0-10% of the dry weight of the particles; preferably the one or more further compounds are present in an amount of 0-5%, preferably 0.1-5%, preferably 0.5-5% of the dry weight of the particles, preferably in an amount of 2-4%. The one or more further compounds are preferably present in an amount of 0.0-1.7%; preferably 0.1-1.7; more preferably 0.2-1; more preferably 0.4-0.8% of the dry weight of the particles. Chitosan is preferably present in an amount of at least 48.3% and preferably at least 50% and more preferably at least 60% of the dry weight of the particles. In one embodiment chitosan is present in an amount of at least 70% of the dry weight of the particles. Where herein the weight of the listed ingredients of the particles in the collection does not add up to 100% the remainder of the weight typically consist of one or more suitable pharmaceutical excipients. Typically, the weight chitosan is chosen such that the weight of the other ingredients together with chitosan makes up 100% of the dry weight of the particles in the collection. In other words the % of the compounds is chosen and the rest is made up of chitosan to get to 100%.

A collection of particles as described herein can have a moisture content of 0-10%; preferably 1-10% of the total weight of the particles, preferably 1-8%, more preferably 1-6% more preferably 1-4% of the total weight of the particles.

The particles in the collection typically have a homogenous composition. A pharmaceutical may comprise two or more different collections of particles, wherein each collection of particles has a homogenous composition that differs from the composition of other collections of particles in the pharmaceutical. Preferably, but not necessarily the one or more other collections are also collections of the disclosure. Multiple collection embodiments are useful for the administration of a two or more active ingredients particularly when two or more of the active ingredients require a different release profile. In cases wherein the pharmaceutical has two or more different collections of particles, at least one of the collections consists of particles having a homogenous distribution of ingredients as specified in the claims and comprising the active ingredient (a protein with a mass of 10 kiloDalton or more, a nucleic acid molecule of 15 nucleotides or more) and the chitosan. In a preferred embodiment the two or more different collections of particles each consist of particles having a homogenous distribution of ingredients as specified in the claims and comprising the active ingredient (a protein with a mass of 10 kilodalton or more, a nucleic acid molecule of 15 nucleotides or more) and the chitosan.

In a preferred embodiment, the collection of particles comprises:
 0.02-25%, preferably 0.2-20%, preferably 0.4-15%, or preferably 1.0-10% of one or more active ingredients of the dry weight of the particles;
 2-25% 2.5-15%, 2.5-12%, 2.5-10%, more preferably 3-8%, preferably 4-6% sucrose of the dry weight of the particles;
 0.2-1% polysorbate 20-80 of the dry weight of the particles;
 0.1-0.3% of one or more amino acids of the dry weight of the particles;
 at least 48.7% and preferably at least 40%, more preferably at least 50% chitosan of the dry weight of the particles.

In a preferred embodiment the collection of particles comprises:
 5-25% of omalizumab of the dry weight of the particles;
 2-25% sucrose of the dry weight of the particles;
 0.2-1% polysorbate 20-80 of the dry weight of the particles;
 0.1-0.3% of one or more amino acids of the dry weight of the particles;
 at least 48.7, preferably 50%, more preferably at least 60% chitosan of the dry weight of the particles.

The weight of moisture in the collection of particles can be as indicated herein above such as, but not limited to 1-10%, preferably about 5-10% of the total weight of the particles.

Particles generated with a method of the disclosure, and collections of particles and pharmaceutical compositions comprising the particles, all refer to so-called solid particles these have a firm interior with a water (moisture) content of preferably 20% or less, preferably 10% or less. Moisture content is typically 1-10% based on the total weight of the particles. The various components of the particle comprising the active ingredient are typically homogeneously distributed in the particle. The particle or collection of particles can, of course be coated, or incorporated into other material.

Further provided is a slow release composition comprising a collection of particles according to the disclosure. The slow release composition can release packed active ingredient when present in the blood stream.

The disclosure further provides a method for delivering a protein of 10 kDa or more, or a nucleic acid molecule of 15 nucleotides or more as an active ingredient, preferably in a therapeutically relevant amount, to the blood of a subject in need thereof, the method comprising preparing a pharmaceutical composition according to the method of the disclosure comprising the protein or the nucleic acid molecule, and orally administering the pharmaceutical composition to the subject. Also provided is a pharmaceutical formulation in oral dosage form, preferably solid oral dosage form comprising a collection of particles of the disclosure for use in the treatment of a disease. The solid dosage form is preferably a tablet, a hard or soft capsule, a caplet, a lozenge, a pill, a mini-tablet, a pellet, or a powder. Non-limiting examples of non-solid dosage forms are a gel, a capsule comprising a fluid or gel and the like.

Further provided is a pharmaceutical composition according comprising a collection of particles as described herein for use in delivering a protein of 10 kDa or more, or a nucleic acid molecule of 15 nucleotides or more as an active ingredient, preferably in a therapeutically relevant amount, to the blood of a subject in need thereof, comprising preparing solid oral dosage form comprising a collection of particles comprising the protein of 10 kDa or more, or a nucleic acid molecule of 15 nucleotides or more as an active ingredient as described herein wherein the oral dosage form is administered orally to the subject.

Further provided is a pharmaceutical composition according comprising a collection of particles as described herein for use in delivering a protein of 10 kDa or more, or a nucleic acid molecule of 15 nucleotides or more as an active ingredient, preferably in a therapeutically relevant amount, to the blood of a subject in need thereof, comprising preparing a solid dosage form comprising a collection of particles comprising the protein of 10 kDa or more, or a nucleic acid molecule of 15 nucleotides or more as an active ingredient as described herein wherein the oral dosage form is administered orally to the subject.

Further provided is a pharmaceutical composition in oral dosage form comprising a particle or a collection of particles as described herein comprising a protein of 10 kDa or more, or a nucleic acid molecule of 15 nucleotides or more as an active ingredient, preferably in a therapeutically relevant amount, for use in the systemic treatment of a disease. The disease is preferably cancer, an immune disease or an infection. Preferably an infection with a micro-organism such as a virus, a (myco)bacterium or a parasite.

The disclosure further provides the use of a particle or a collection of particles comprising a protein of 10 kDa or more, or a nucleic acid molecule of 15 nucleotides or more as an active ingredient for the manufacture of a medicament for oral delivery of the active ingredient. The disclosure further provides the use of a particle or a collection of particles comprising a protein of 10 kDa or more, or a nucleic acid molecule of 15 nucleotides or more as an active ingredient for the manufacture of a medicament in an oral dosage form.

Particles of the disclosure are preferably packaged into a system suitable for oral delivery of medicaments to the intestinal tract. Such methods include but are not limited to enteric coating of a tablet or pill, a delayed release formulation and a capsule that is resistant to an acidic environment. After protection to the gastric low pH, the remaining digestive tract contains systems like absorptive enterocytes in the microvilli. An active transport mechanism over the intestinal wall can potentially be targeted for particle uptake. Particles of the disclosure facilitate release of the biological molecule from the particles into the blood stream. Without being bound by theory it is believed that particles migrate at least partially intact through the intestinal wall.

The diameter of a nearly spherical particle can be determined by determining the longest axis through the particle and selecting the perpendicular cross section with the highest surface area and selecting the distance of the longest line through two points on the edge of the surface.

A preferred method of measuring a diameter of a particle is by TEM (Transmission Electron Microscopy) or by SEM (Scanning Electron Microscopy).

The term "moisture" as used herein refers to water in the particle. This water is typically not present in free form but associated with otherwise dry material in the particle.

For the purpose of clarity and a concise description features are described herein as part of the same or separate embodiments, however, it will be appreciated that the scope of the disclosure may include embodiments having combinations of all or some of the features described.

EXAMPLES

Example 1

After protection to the gastric low pH by, for instance, enteric coating of the particles, stomach passing tablet with the particles or capsules containing these particles; the remaining digestive tract contains systems like absorptive enterocytes in the microvilli, for selective molecules an active transport mechanism over the gut wall, systems that potentially can be targeted for particle uptake and subsequent release of the biological present in the particles to be released into the blood stream.

Particles of the disclosure can have the property that little protein is released in the first part of the gut (pH 8). The particles allow transport over the walls of the intestines. Once in the blood circulation the active ingredient is released (pH 7.4). Preferably, the release profile for the active ingredient in blood is a sustained one. This means the active ingredient is released over a prolonged period.

The oral delivery of biologically active macromolecules (biologics) has been a challenge thus far and moderately successful for small biologics only, like insulin with a molecular size of <6 kDa resulting in a low bioavailability.

Table 1 shows non-limiting examples of macromolecules of potential interest for oral formulation and their kDa.

TABLE 1

| Macromolecule | approx. MW (kDa) |
|---|---|
| Insulin | 6 |
| Calcitonin | 3 |
| Interferon alpha-2a | 17 |
| Erythropoietin | 21 |
| Monoclonal antibodies | 146 |
| Antisense oligonucleotide | 6 |
| Factor VIII | 280 |
| Factor IX | 56 |
| Von Willebrand factor | 800-20,000 |
| TNF | 26 |
| GH | 22 |
| Etanercept (Enbrel) | 150 |
| Fusion proteins | 75-500 |
| Prolidase | 108 |

Biologics having a kDa ranging from 10-500 kDa are currently delivered by intravenous or subcutaneous injection only, while the oral route is highly preferred for chronic therapies.

The low bioavailability (<10%) of peptides and proteins in oral formulations, initiated the use of permeation enhancers with mixed results.

Materials and Methods

The technology used in this disclosure for encapsulation of complex macromolecules is based on a supercritical carbon dioxide technology as an alternative way to create solid formulations for biologicals.

The premise of this technology is that at elevated temperature and pressure (30° C./73 Bar) CO2 becomes supercritical, i.e., "is in a supercritical state." Under these conditions CO2 combines the high diffusivity of a gas with the solvation capacity of a liquid.

Specialized dedicated equipment is used in this technology, able to safely withstand high pressure and capable of varying several parameters while spraying aqueous compositions into a pressure chamber where CO2 is at supercritical state.

FIG. 1

Through this method solid particles can be obtained by spraying an aqueous composition containing protein and excipients through a nozzle. Subsequently, $scCO_2$ efficiently extracts the solvent and results in a completely solvent-free powder with a narrow diameter distribution. The waste CO2 contains the water fraction.

The diameter of these particles can range from nanometer (nm) to micrometer (μm).

The relatively mild conditions of the anti-solvent process permit the creation of dried protein particle formulations with high retention of biological activity.

Powder characteristics can be tuned by control of various parameters (pressure, temperature, nozzle dimensions, solution flow-rate, $CO_2$ flow-rate, concentration of protein, and the nature and concentration of excipients).

TABLE 2

Adjustable equipment settings for the preparation of particles

| | | |
|---|---|---|
| CO2 pressure | 100-180 | Bar |
| CO2 temperature | 40-50° C. | |
| CO2 flow rate | 150-350 | kg/hr |
| Solution flow rate | 2-8 | ml/min |

TABLE 3

Variables in the composition of the fluid to be sprayed

| | |
|---|---|
| Chitosan, deacetylation 60-90%; Viscosity 20-500 CPS | 1-10% |
| Aminoacids | 0.001-0.005% |
| Sucrose | 0.01-0.25% |
| Polysorbate PS 20-80 | 0.001-0.005% |
| Sorbitan stearate | 0.001-0.005% |
| Biologically active molecule | 0.01-0.5% |

Before spraying this chitosan was first dissolved in water acidified with acetic acid (pH3). Immediately before spraying the protein was subsequently dissolved in this solution.

Dried powder encapsulates were trapped on a filter at the bottom of the vessel and collected manually at the end of the experiment. Dried powders were stored in a refrigerator (2-8° C.) until further characterization.

Protein Release testing

Powder (20 mg for BCA or 200 mg for HPLC testing) are weighed into a test tube. To each tube a volume (1 ml for BCA testing or 10 ml for HPLC testing) release medium is added. Release medium is either PBS pH 7.4 as a buffer system that mimics pH of blood or phosphate buffer pH 8 as a buffer system that mimics pH of the gut.

Tubes with particle suspension are kept at 37° C. on a roller bank. Sampling is done at 0.5; 1; 1.5; 2; 4; 7; 17 and 24 hr (unless otherwise indicated). At each sample point, 50% of the release medium is withdrawn from the tube (after brief centrifugation to precipitate the particles) and 50% fresh medium is added to the suspension for continuation of the release test.

Protein levels are determined using a QuantiPro BCA assay kit or HPLC.

Results

Cytokine Interferon-Alfa-2a (IFN)

Studies on commercially available biosimilar interferon alpha-2a (IFN) embedded in particles.

Aqueous solutions of chitosan were sprayed into supercritical CO2. Chitosan was dissolved in water acidified with acetic acid (pH3). Immediately before spraying the IFN was dissolved.

| Composition of fluid sprayed | |
|---|---|
| Chitosan, deacetylation 77%; | 3% |
| Acetic acid | 0.5% |
| Sucrose | 0.1 |
| Polysorbate PS 20 | 0.001 |
| Biologically active molecule: IFN | 0.2% |

| Equipment settings for the preparation of particles | |
|---|---|
| CO2 pressure | 150 Bar |
| CO2 temperature | 50° C. |
| CO2 flow rate | 300 kg/hr |
| Solution flow rate | 2.5 ml/min |

Materials were characterized for particle diameter (SEM; DLS), load of IFN (HPLC) and release of IFN. Structural integrity was tested using SDS-PAGE.

Spray Drying into $scCO_2$

Spraying experiments were conducted on a 1 to 2 gram solids scale. The ratio of polymer to protein (IFN) was 99 to 1 percent. The solids were dissolved in 60 gram water.

Powder yields (amount of solids recovered) in these small-scale spraying experiments were typically between 40 and 80 percent.

Figure 2:
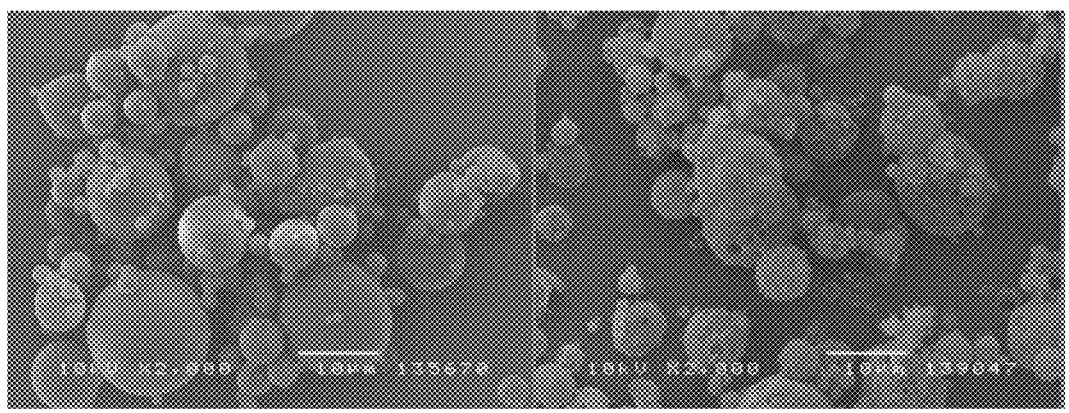
FIG. 2 Chitosan particles. 1% IFN in Chitosan.

Powder Characterization (SEM) FIG. 2

Scanning Electron Microscopy (SEM) characterization on the powders showed that a chitosan-based powder yielded spherical particles varying between 1 and ten micron in diameter.

Protein Load in the Particles.

For Chitosan based particles, it proved possible to dissolve the Chitosan by incubation of the particles in pH 4 acetate and obtain a solution that was injectable in the HPLC for determination of the IFN in the particles.

Two different batches of 1% IFN in Chitosan were dissolved in triplicate. Results are shown in Table 4.

TABLE 4

IFN loading efficiency for chitosan particles.

| Batch | Average load efficiency | RSD % |
|---|---|---|
| 1 | 47% | 8.1 |
| 2 | 46% | 15.3 |

Protein Release Testing

Figure 3:
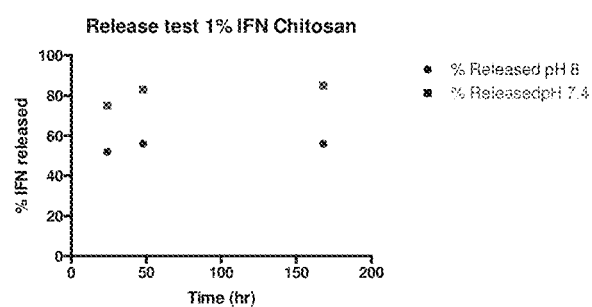
FIG. 3 IFN release measured by HPLC from Chitosan.

Protein release tests were performed using the BCA protein assay. Particles generated appeared to release up to 80% IFN within 24 hours at pH 7.4 using a BCA assay. FIG. 3

Stability of the IFN Chitosan particles was demonstrated for a period of one year.

Figure 4:
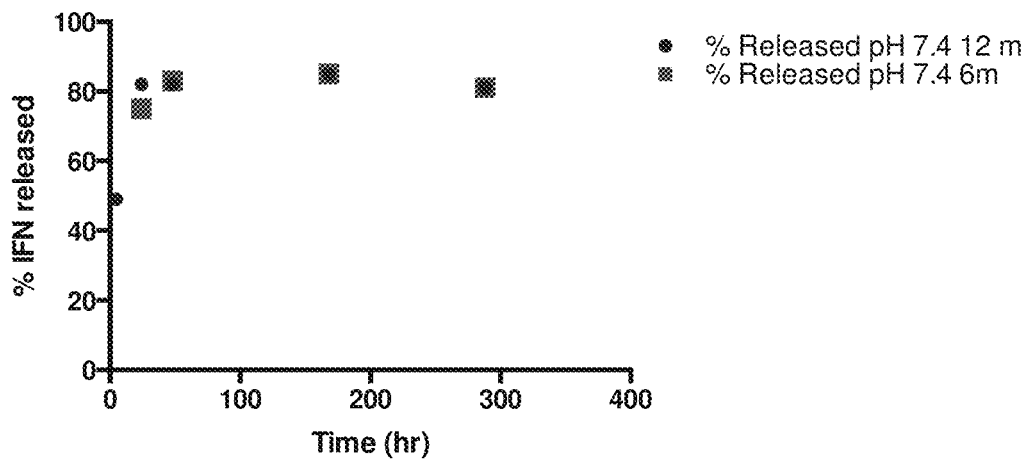
FIG. 4 Stability of Interferon Chitosan particles after 6 and 12 months at room temperature.

Particles retained a consistent release profile after a storage period of one year. FIG. 4

Conclusions

Particles with encapsulated interferon alpha-a could be produced using $scCO_2$ technology with good reproducibility with respect to release profile and loading efficiency.

Monoclonal Antibody Omalizumab

Studies on Omalizumab Embedded in Particles

Aqueous solutions of chitosan were sprayed into supercritical CO2. Chitosan was dissolved in water acidified with acetic acid (pH3). Immediately before spraying the antibody (Omalizumab) was dissolved.

TABLE 5

Composition of fluid sprayed

| | |
|---|---|
| Chitosan, deacetylation 77%; | 8% |
| Amino acids | 0.015% |
| Sucrose | 1% |
| Polysorbate PS 20 | 0.01% |
| Biologically active molecule: omalizumab | 0.9% |

TABLE 6

Equipment settings for the preparation of particles

| | |
|---|---|
| $CO_2$ pressure | 150 Bar |
| $CO_2$ temperature | 50° C. |
| $CO_2$ flow rate | 300 kg/hr |
| Solution flow rate | 2.5 ml/min |

Materials were characterized for particle diameter (SEM; DLS), load of Omalizumab (HPLC) and release of Omalizumab. Structural integrity was tested using ELISA and SDS-PAGE.

Load of Omalizumab 5 mg particles were dissolved in 1.5 ml pH 4 acetate by rolling in a stove at 37° C. overnight or longer. Upon dissolution the solution was filtered over 0.45 μm filter to remove any sub-visible particles before analysis by HPLC.

Release of Omalizumab 10 mg Particles were suspended in PBS (mimic release in blood) or pH8 phosphate buffer to mimic release in the gut. The suspensions were kept rolling at 37° C. At given time intervals the clear buffer was pipetted from the top of the particles and filtered over 0.45 μm before analysis by HPLC.

Elisa

ELISA was performed using a commercially available kits. Based on concentrations determined by HPLC, samples were diluted to a quarter of the concentration of the highest calibrator.

SDS-PAGE

Approximately 2 μg protein was loaded into the slots of a 4-20% Tris HCl gel. The gel was run at 90 V for 5 minutes after which a voltage of 180 minutes is applied. The total run time was 45 to 60 minutes. The gels were stained using Coomassie brilliant blue.

Results

Particle Load

Load of the particles in the initial experiments was set at 16% of chitosan, and showed that the actual load of 14% could be measured practically.

ELISA

The biological integrity, based on the ELISA results, seems to be intact after encapsulation and subsequent release

SDS-PAGE

Figure 5:
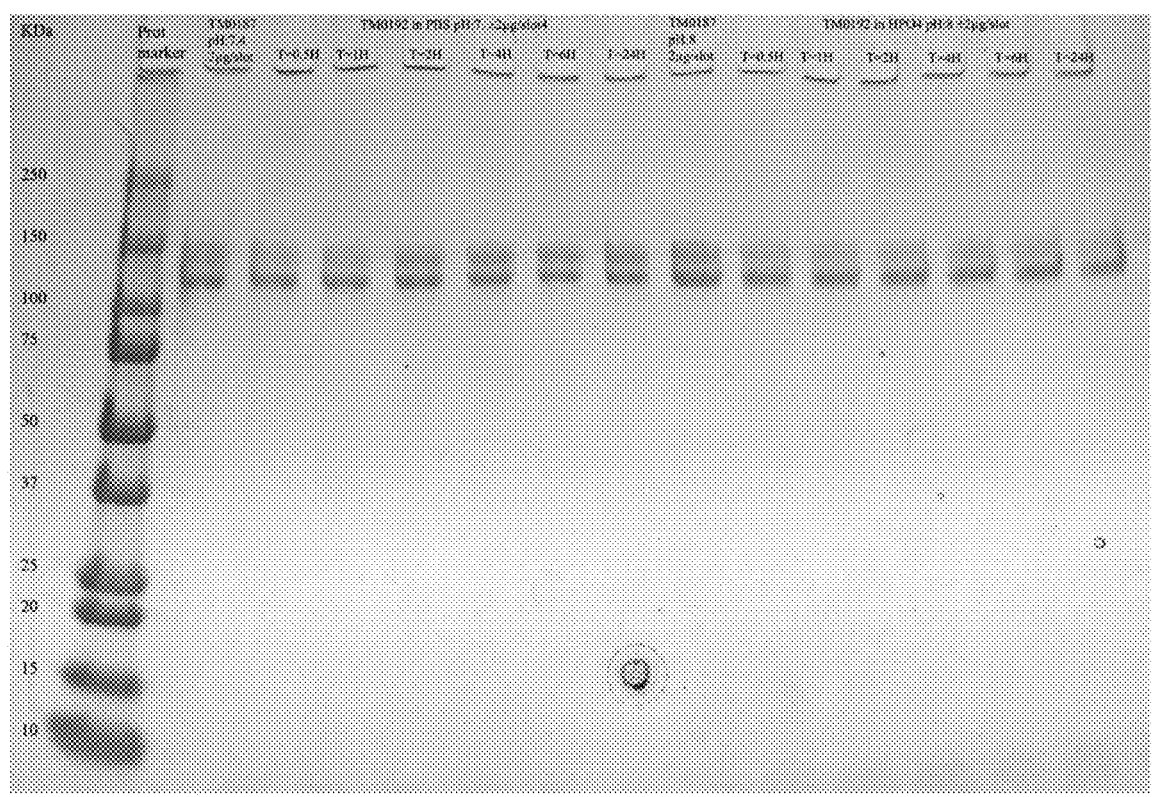
FIG. 5 SDS-PAGE shows that Omalizumab clearly remained intact.

From this experiment omalizumab (TM0192) clearly remained intact. FIG. 5

Particle Diameter and SEM

Particle diameter was determined using Dynamic Light scattering (DLS).

For the majority of the particles produced, particle diameter is around 500 nm.

Figure 6:
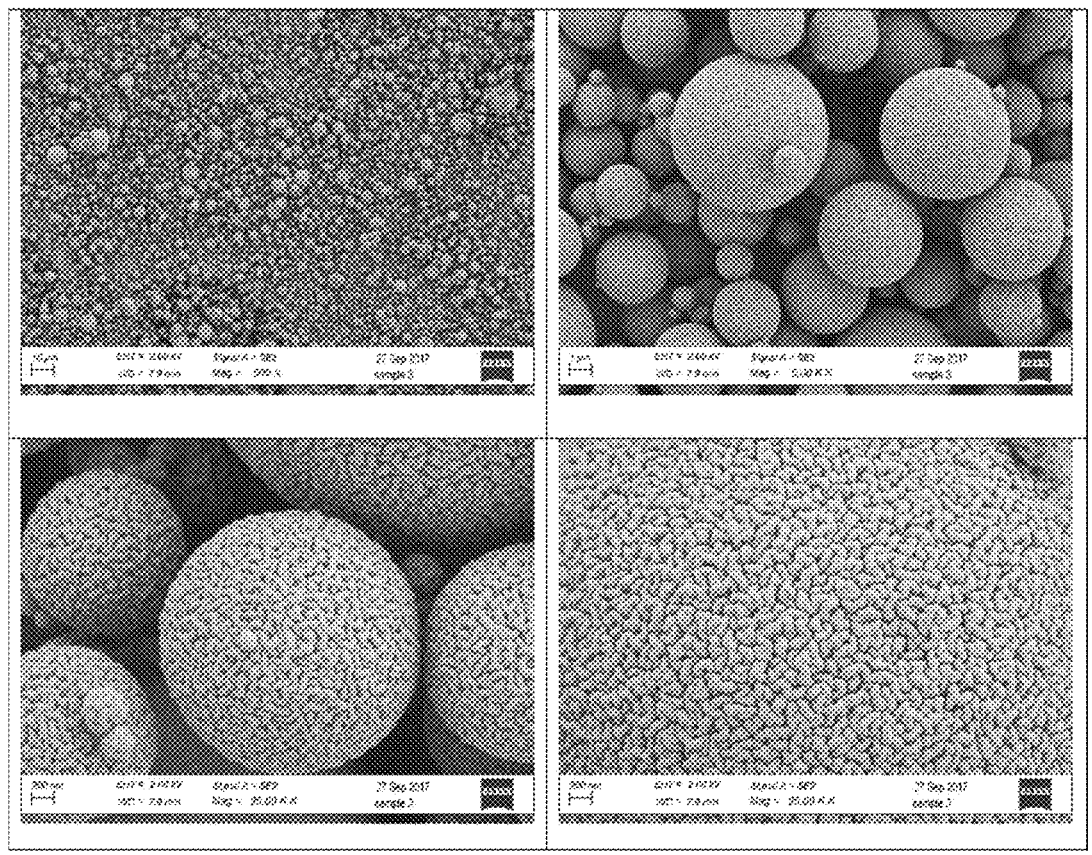
FIG. 6 Scanning electron microscopy revealed spherical particles.

SEM in FIG. 6 shows the particles

Bioavailability in Rat

To evaluate the bioavailability of encapsulated Omalizumab in rat after intraduodenal administration, rats were dosed intraduodenally.

Figure 7:
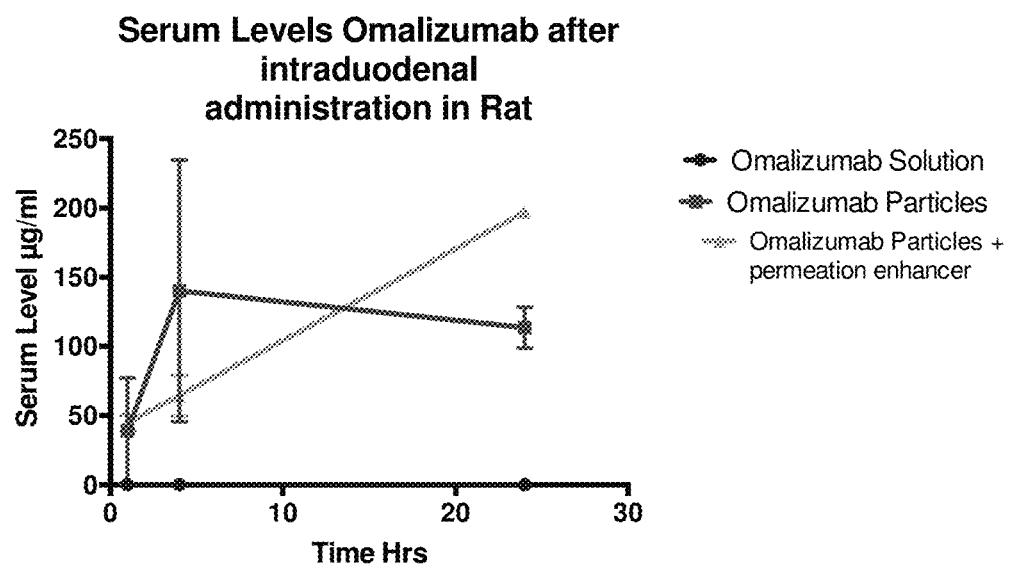
FIG. 7 Serum levels Omalizumab after intraduodenal administration in Rat.

18 Rats were divided into three groups. Group 1 was administered 0.2 ml of a solution of Omalizumab (5 mg/ml). Group 2 and 3 were administered with a 200 μl of suspension of Omalizumab particles (10 mg/ml) suspended in buffer (group 2) and buffer with a permeation enhancer (group 3). At the end of the experiment rats were sacrificed and bloodserum was collected. Serum was collected after 1; 4 and 24 hours (each time point in duplicate). Serum Levels of Omalizumab were determined ELISA kit. FIG. 7

It shows that with the current particle diameter the encapsulated protein is taken up by the gut and subsequently released in the blood.

The possible effect of permeation enhancers was probably masked by the large basal uptake. No significant effect was seen of the permeation enhancer.

This can be explained by the already high bioavailability of the antibody included in the chitosan particles. Chitosan itself is known to be a permeation enhancer by itself Conclusions Particles with encapsulated omalizumab could be produced using $scCO_2$ technology with good reproducibility with respect to release profile and loading efficiency.

In addition, the chemical and biological integrity of the omalizumab molecule seems to be intact based on HPLC and ELISA data.

Moreover, a preliminary rat study showed that blood levels of omalizumab could be detected in the omalizumab encapsulated particle applied group and not in the group of omalizumab applied without encapsulation.

The results obtained in this project indicate that $scCO_2$-assisted chitosan-encapsulation technology can be applied in the development of stable formulations of macromolecules to be used in oral formulations.

Example 2

Evaluation of BiOraliX' manufacturing process on protein structure and functionality of omalizumab Introduction A series of tests was done to assess the structure, composition and functionality of omalizumab before and after application of the process, i.e.:

Structure: circular dichroism, N-glycans, Peptide maps, Intact mass,

Disulfide Bridges

Analytical (aggregation/particle diameter): SV-AUC

Functional: SPR biding kinetics and potency (ELISA based)

Samples

1. The antibody used for this purpose was omalizumab. This monoclonal antibody was manufactured in a fermentation process using Canine Hamster Ovary cells, and purified to obtain >95% purity. This drug substance (DS) was kept frozen (−20° C.) until further processing.

Sample 1 is the DS sample as described above

Figure 8:
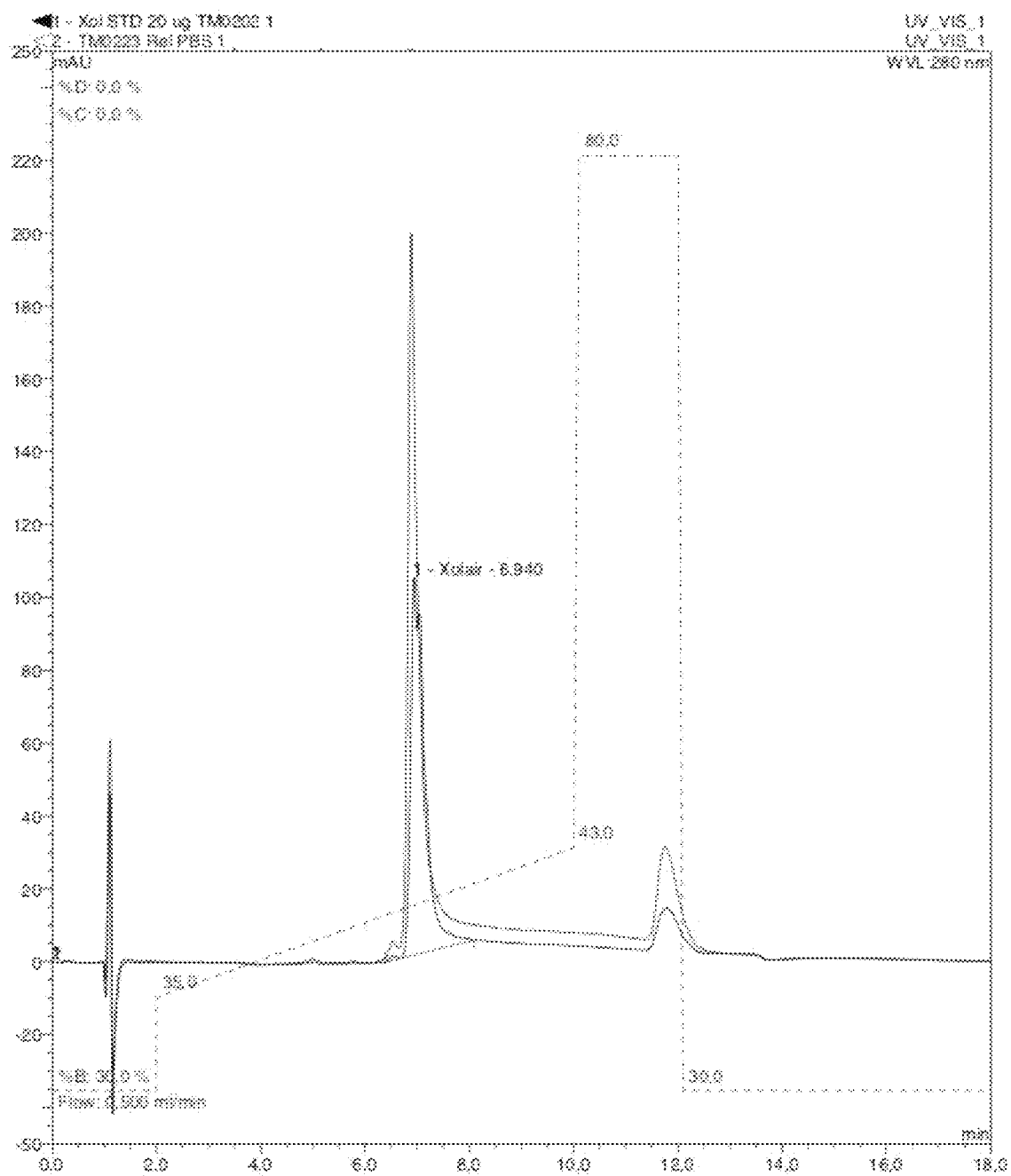
FIG. 8 HPLC profile overlays of reference Omalizumab and released Omalizumab
Figure 9:
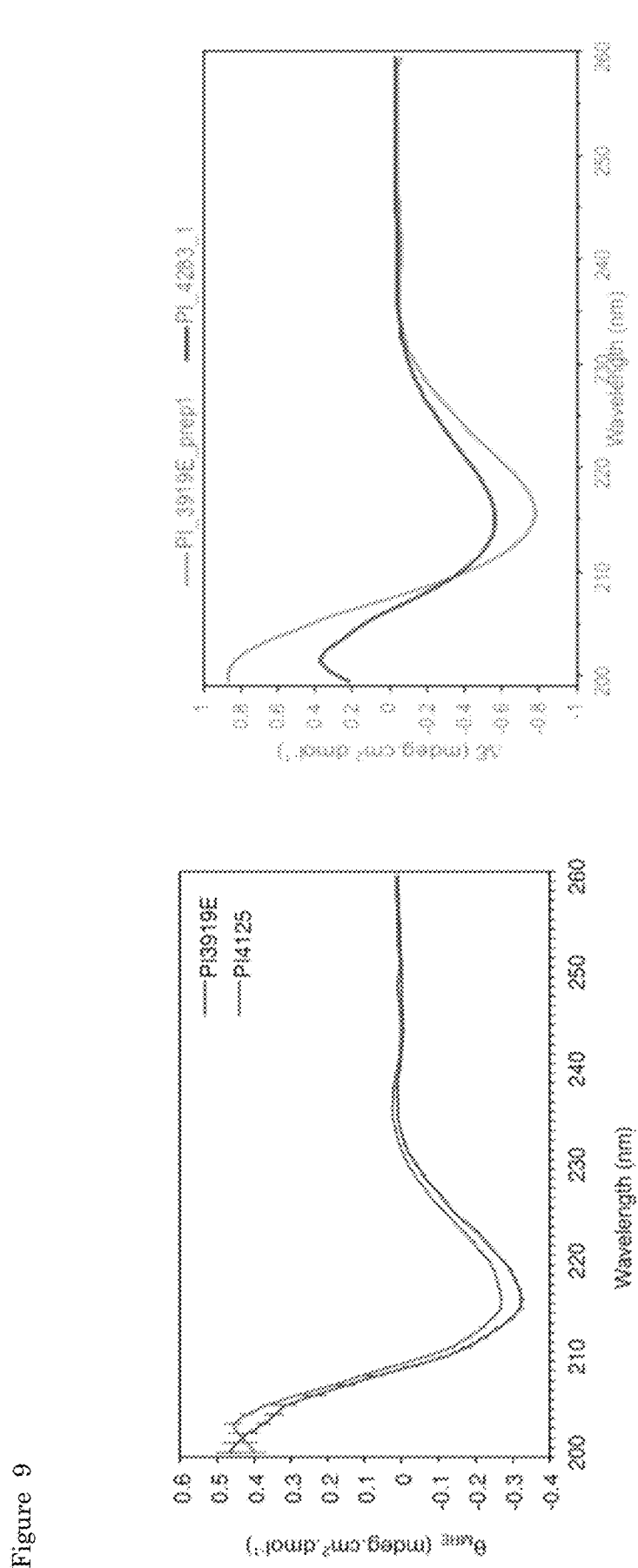
FIG. 9 CD analysis
Figure 10:
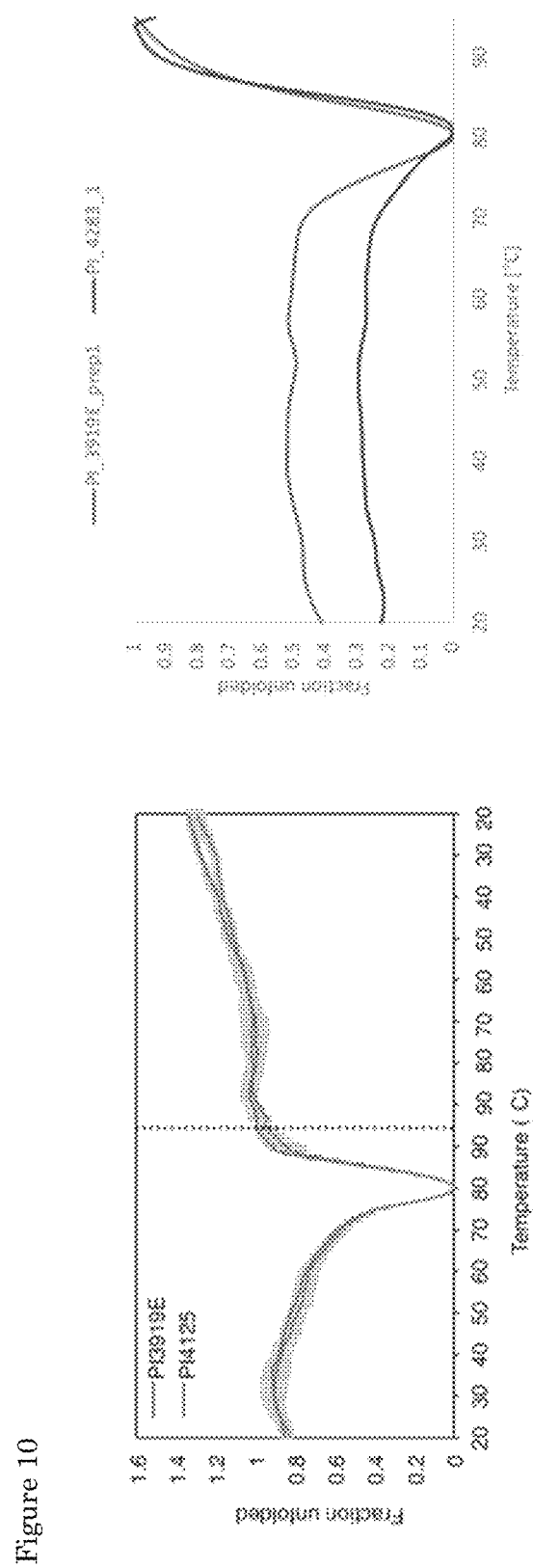
FIG. 10 Melting curve analysis
Figure 11:
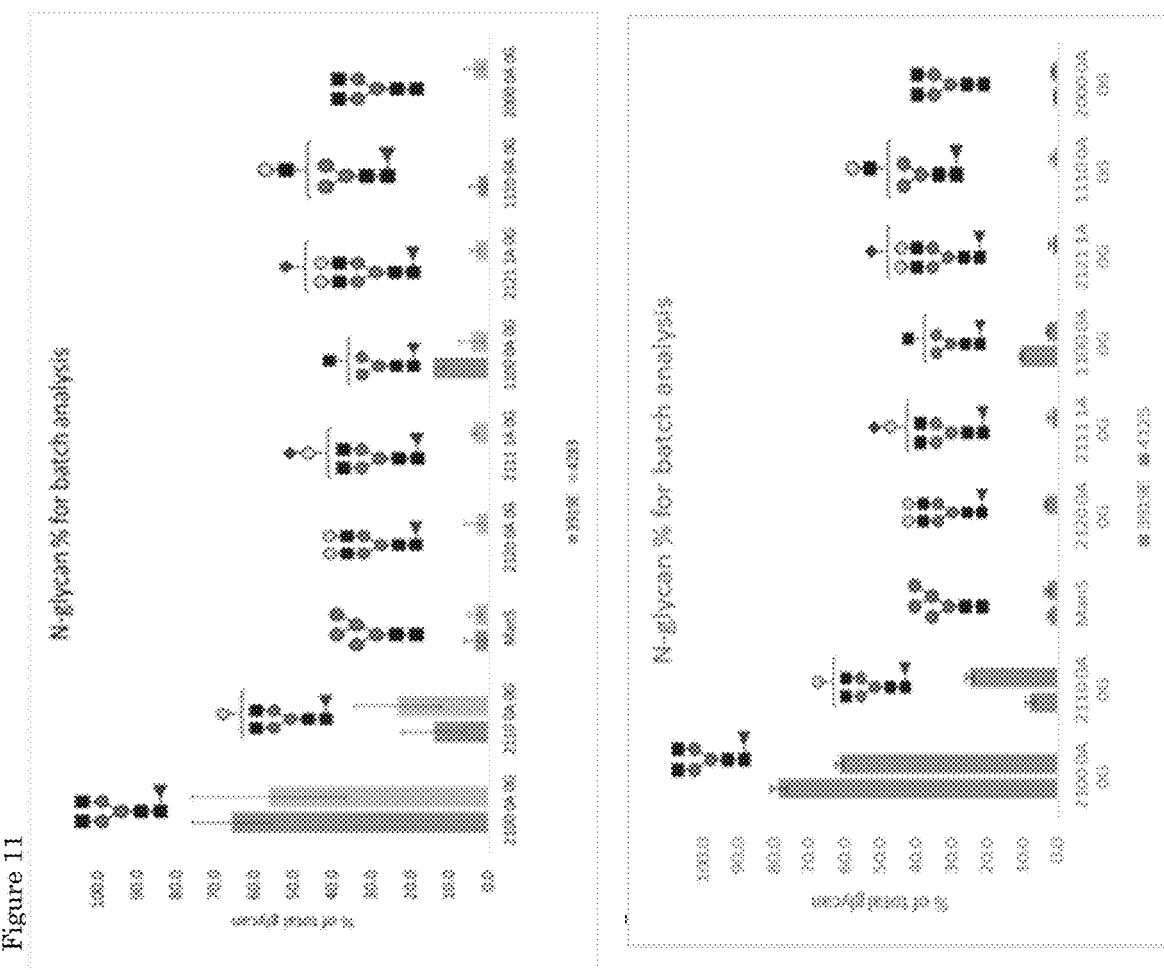
FIG. 11 N-glycan % for batch analysis
Figure 12:
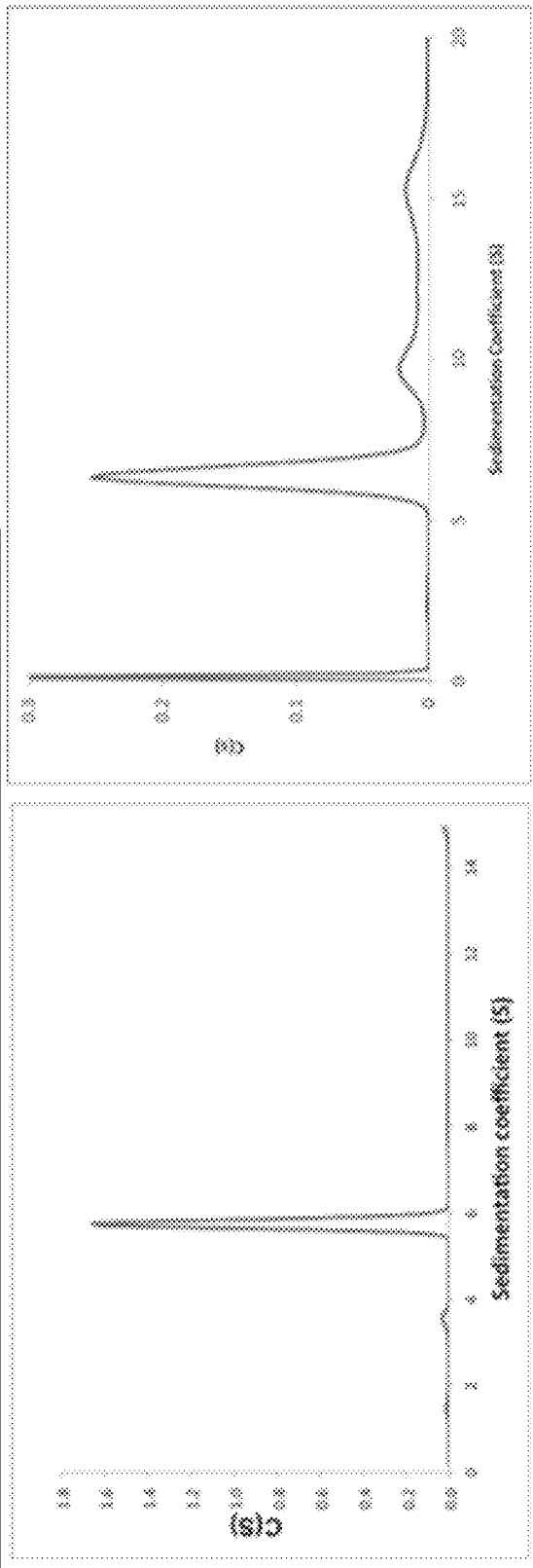
FIG. 12 Continuous sedimentation coefficient distribution for sample 1 (left) and 2 (right)
Figure 13:
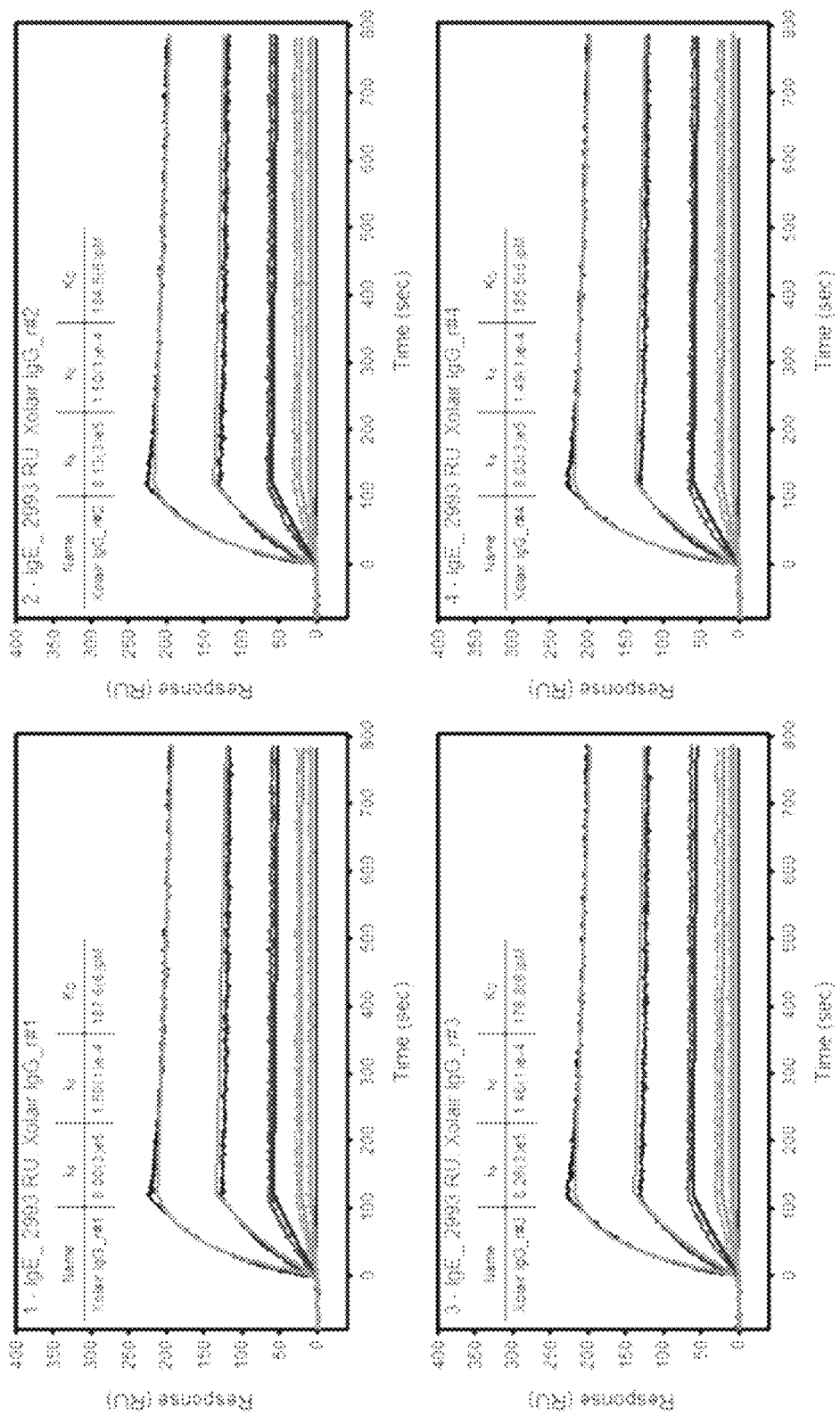
FIG. 13 SPR interaction analyses between injected Xolair IgG (t=0) and amine coupled IgE surface in Lane 5 (contains 2993 RU of protein)
Figure 14:
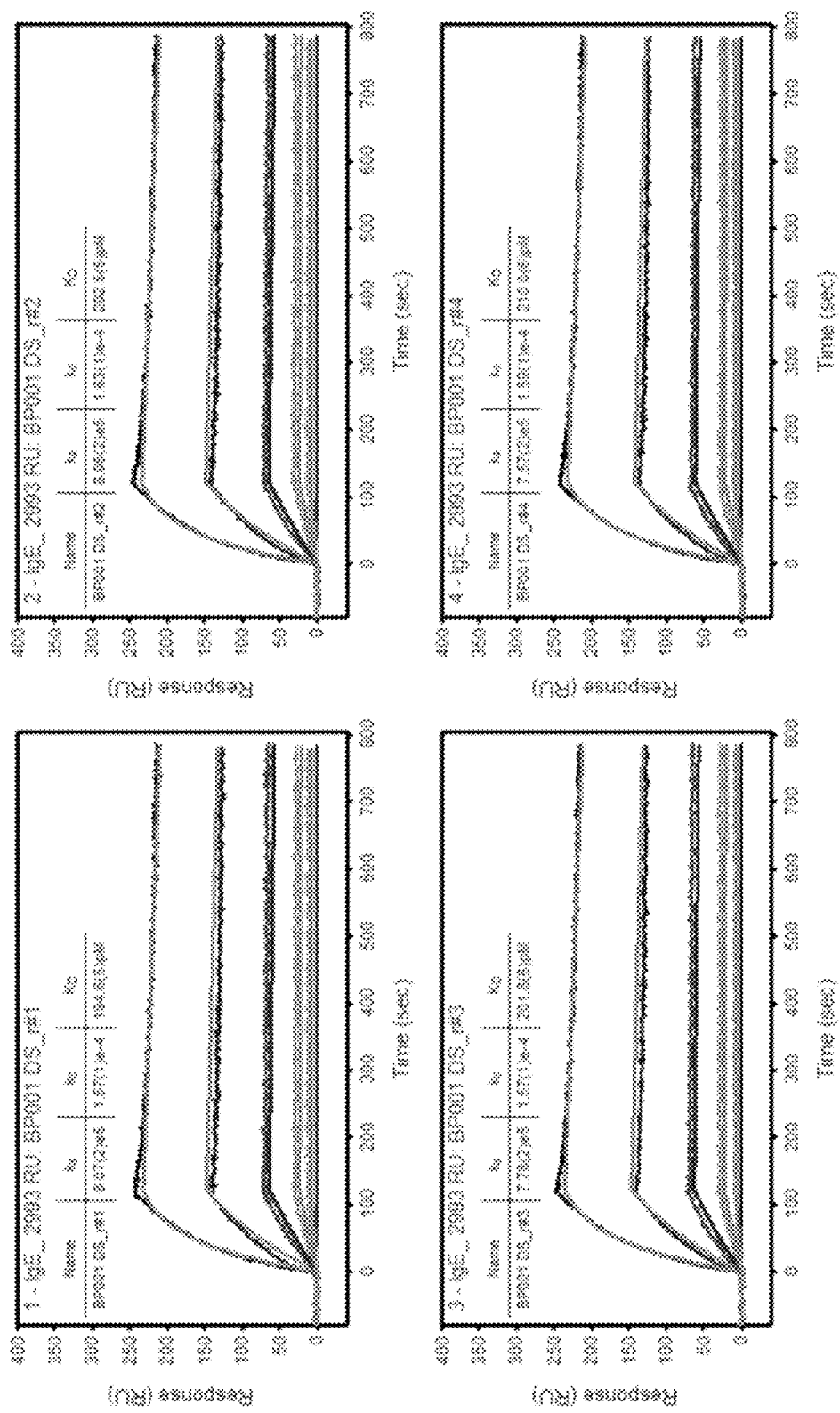
FIG. 14 SPR interaction analyses between injected BP001 DS IgG sample (t=0) and amine coupled IgE surface in lane 5 (contains 2993 RU of protein)
Figure 15:
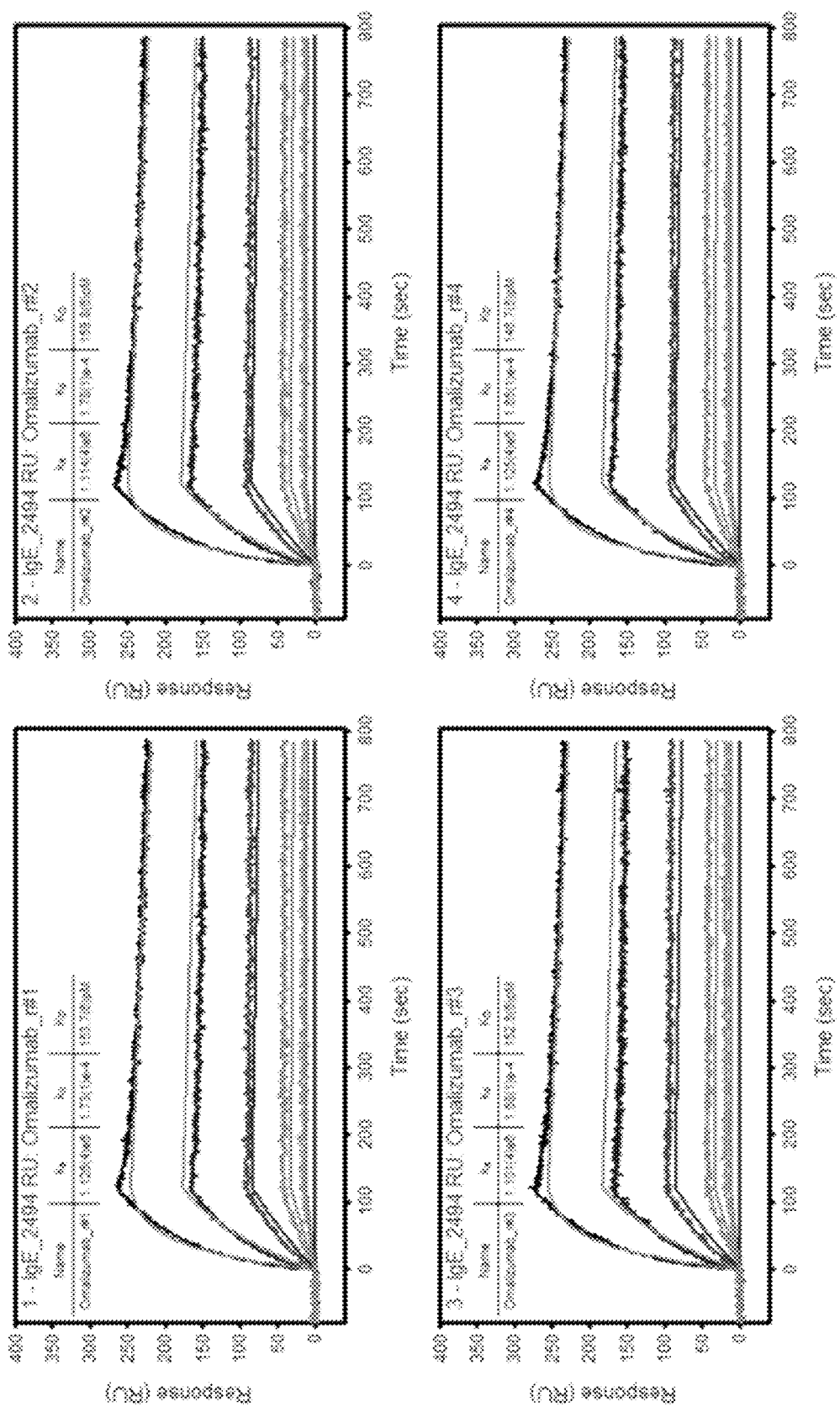
FIG. 15 SPR interaction between injected Omalizumab (t=6 months) and amine coupled IgE surface in Lane 6 (contains 2494 RU of protein FIG. 16 SPR interaction between injected BP001 "DPinPBS" sample and amine coupled IgE surface in Lane 6 (contains 2494 RU of protein.
Figure 16:
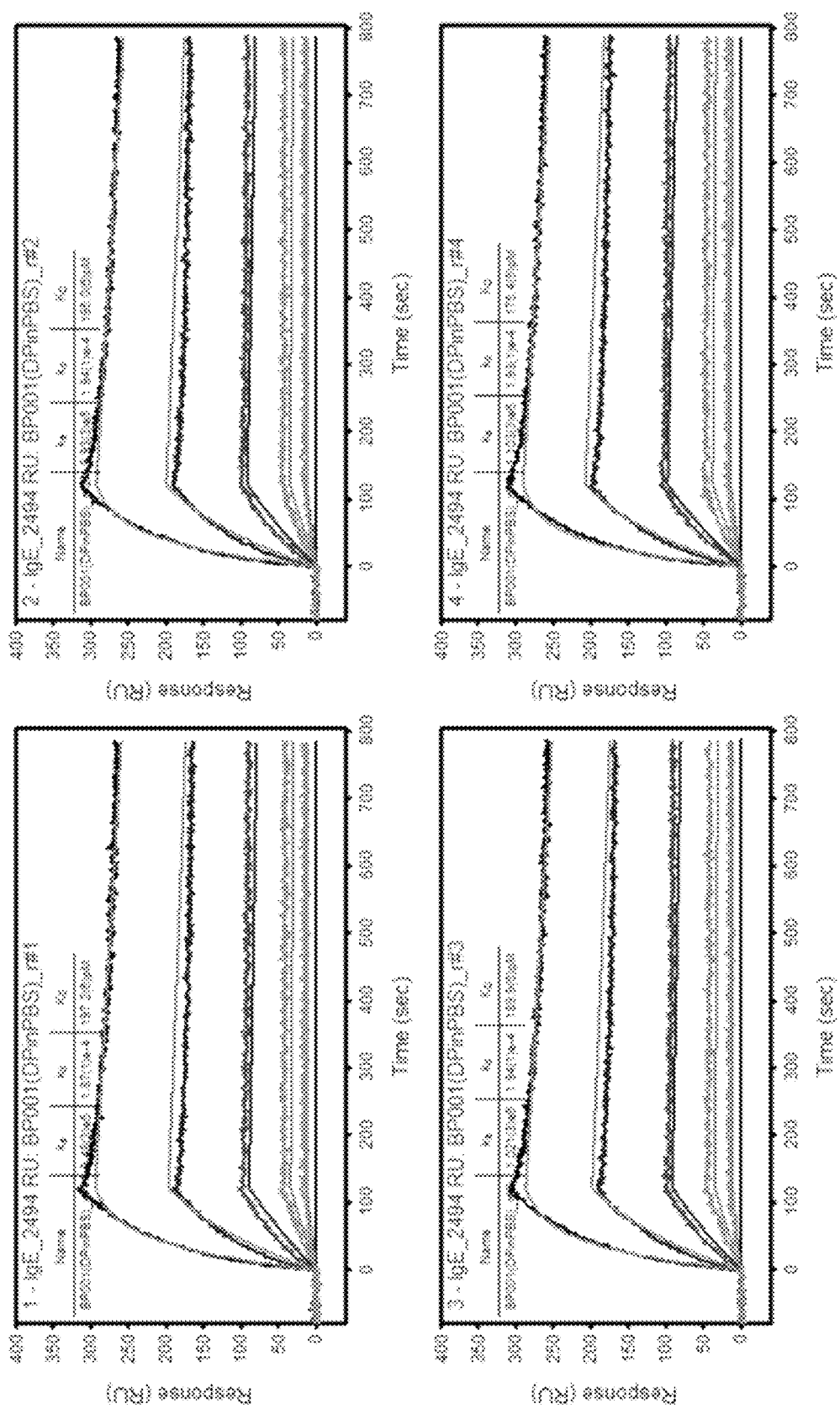

Sample 2 was a sample after the above mentioned DS was exposed to the disclosure and further processed after the following procedure:

the obtained particles were released in PBS buffer and frozen before shipment samples were sent to external laboratories for characterization and comparisons FIG. 8 is an HPLC trace of sample 2 as compared to the originator version of omalizumab (XOLAIR®) and shows that the identity of both active ingredients in the samples is the same.

A summary of the activities (functional, binding and analytical characteristics) conducted on the base material (for which sample 1 is representative) and the material for which sample 2 is representative is provided in the next TABLE and FIGS. 9-16

The 2 samples have been analyzed in two independent occasions, however in both occasions the same reference sample (XOLAIR®) was analyzed in order to bridge data and be able to compare.

| Property | Lab | Method | Result | | | | | Reference |
|---|---|---|---|---|---|---|---|---|
| Structure analytics | PILL | Circular dichroism | | PI-3919E (ref for sample 2) | PI-4125 (sample 1) | PI-3919E (ref for sample 2) | PI-4283 (sample 2) | Reports: R171030BPSH_CD_Final and |
| | | | α-helical (%) | 0.0 ± 10 | 0.0 ± 10 | 0.0 ± 10 | 0.0 ± 10 | R180302BOSH_CD_draft |
| | | | Beta-sheet (%) | Not determined | Not determined | 100.0 ± 10 | 75.9 ± 10 | Appendix 2 |
| | | | Random coil (%) | Not determined | Not determined | 0.0 ± 10 | 24.1 ± 10 | |
| | | | Melting temperature (° C.) | 72.5 ± 0.9 | 71.9 ± 1.6 | 73 | 64 | |
| N-glycans | PILL | LC-MS/MS | Conclusion: The Circular Dichroism spectral line shapes of the reference sample PI-3919E were different to test sample PI-4283 under the conditions applied, for sample 2 values for melting point slightly differ N-glycan patterns in sample 1 and 2, absolute and relative to the same reference sample, are similar. | | | | | Reports: GA171110BPSB_N_Glycan_4125_reissued and GA180222BPSH_NGlycan_4283_Draft Appendix 3 |
| Intact mass | PILL | TOF-MS | Intact mass was determined before and after deglycosylation, and in reduced and non-reduced form, and using XOLAIR ® as reference. Glycosylated non-reduced mass determined was 149 kDa for both samples. Deglycosylated non-reduced mass determined was 146 kDA for both samples, although sample 2 showed other major species. Molecular mass of the light chain for both samples was 23,899 Da, which is in agreement with the theoretical mass (23,900 Da). Molecular mass of appr. 50.7 kDa was observed for the heavy chain for all samples measured. For sample 2 however, other major species were observed. The mass difference between the untreated and enzyme treated heavy chain was approximately 1,440 Da for both samples measured (and the reference). This mass difference corresponds to the major glycan that was observed during N-glycan analysis. Overall conclusion; both samples were similar for the main component, but samples 2 showed various other major species, which might be originating from degradation, modification or aggregation | | | | | Reports: M171030BPSH_Intact_Final and M180222BOCA_4283_Draft |
| Aggregation | PILL | SV-AUC | Sample | Weight average sedimentation coefficient (S) | Proportion of total signal (%) | | Frictional ratio | Reports: R171030BPSH_AUC_Final and |
| | | | 1 | 3.7 | 2.5 | | 1.88 | R180221BOKR_AUC_Draft Appendix 4 |
| | | | | 5.7 | 97.5 | | | |
| | | | 2 | 6.3 | 61.1 | | 1.5 | |
| | | | | 9.7 | 16.6 | | | |
| | | | | 15.2 | 15.7 | | | |
| | | | Discussion on the different profiles Re the S = 10 peak, this is something seen regularly in the Omalizumab profiles. The new peak is the one at S = 15, which is not appearing in the control (3919E) sample, which is the indications of the differences between samples. Re the relative lack of the S = 10 peak in the DS t = 0 m (4125) sample and the new occurrence of the peak at S = 3.5 then this is somewhat of a new profile for omalizumab given what we've seen previously. There isn't a great explanation for why this occurred - the records indicate the same protocol was followed and the data has been presented as its generated. Given it's a lower sediment coefficient (S) then it's possible it's due to a contaminant, which would have to be a smaller molecule than omalizumab, entering in the common steps of both samples. However, it's present in both the control and the 4125 samples suggesting sample and control are similar in aggregation properties. | | | | | |
| Peptide mapping | PILL | LC-MS/MS | For sample 1 and the simultaneously analyzed reference, the protein sequence coverage for both the reference and test samples for the heavy chain was 95%; for sample 2 and the reference this was 92% and 94% For sample 1 and sample 2 and the simultaneously analyzed references, the protein sequence coverage for both the reference and test samples for the light chain was 100% Evidence of N-terminal pyro-glutamination was observed in both the heavy chain of the reference and samples 1 and 2. Evidence of C-terminal truncation of a lysine residue was observed in both the heavy chain of the reference and samples 1 and 2. Conclusion: peptide mapping results were similar for both samples, with slight variation in the heavy chain | | | | | Reports: PM171010BPSH_Mapping_Final and PM180208BPKR_4283_Mapping_Draft |

-continued

| Property | Lab | Method | Result | Reference |
|---|---|---|---|---|
| Disulfide bridges | PILL | LC-tripleTOF MS | For both samples, the following postulated Cys bridges were confirmed: Cys22(H)-Cys96(H) Cys148(H)-Cys204(H) Cys265(H)-Cys325(H) Cys371(H)-Cys429(H) Cys23(L)-Cys87(L) Cys133(L)-Cys193(L) Cys230-Cys230(H) and Cys233-Cys233(H)<br>For both samples, the remaining interchain disulfide bridge Cys218(L)-Cys224(H) was not confirmed by mass spectrometry analysis samples, but could be inferred from the collective results.<br>Conclusion: no difference in disulfide bridges between sample 1 and 2 | Reports: DS171010BPSH_DS_Final and DS180222BOJL_4283_Draft |
| Potency | VIP | | Sample 1: potency, relative to a randomly selected XOLAIR ® lot was 85.6% on average (3 replicate ranging from 61.4% to 107.5%)<br>Sample 2: potency, relative to the same XOLAIR ® lot as sample 1 was 82.1% on average (3 replicate ranging from 69.6% to 97.6%)<br>Conclusion: potency for sample 1 and sample 2 comparable, with comparable range from triplicates | Reports: vivoPharm BIPV0010:008:2328 and vivoPharm BIPV0010:2339 |
| Binding kinetics | CSIRO (on behalf of VIP) | Surface Plasmon Resonance | Kinetic rate & affinity constants for IgG samples interacting with immobilized IgE: (see table below)<br>Conclusion: binding kinetics for sample 1 more comparable to reference than sample 2; binding profiles are comparable with reference for both samples, and binding profiles of | Reports: CSIRO report BIPV0011: SPR Stability Testing Study of IgG-IgE Interaction (t = 0) CSIRO report BIPV0011: SPR Stability Testing Study of IgG-IgE Interaction: t = 6 months Appendix 5 |

| | $k_a \times 10^5$ ($M^{-1}s^{-1}$) | $k_d \times 10^{-4}$ ($s^{-1}$) | $k_D$ (pM) | $R_{max}$ (RU) |
|---|---|---|---|---|
| Xolair as ref for Sample 1 | 8.1 ± 0.1 | 1.49 ± 0.02 | 184 ± 5 | 233 ± 3 |
| Sample 1 | 7.9 ± 0.2 | 1.59 ± 0.03 | 202 ± 6 | 254 ± 2 |
| Xolair as ref for Sample 2 | 11.2 ± 0.1 | 1.17 ± 0.06 | 153 ± 5 | 259 ± 5 |
| Sample 2 | 10.2 ± 0.7 | 1.92 ± 0.03 | 189 ± 10 | 304 ± 5 |

Conclusions

The data collected for sample 2 (untreated protein processed into particles and released in PBS) show great similarity with the data collected for sample 1 (untreated protein).

Analytical, structure and functional tests have shown that the molecule is intact and functional.

Example 3

Evaluation of BiOraliX' Manufacturing Process on Protein Structure and Functionality of Omalizumab Introduction A series of tests was done to assess the structure, composition and functionality of omalizumab before and after application of the process, i.e.:
- Structure: Circular dichroism, Peptide maps, Intact mass, Disulfide Bridges
- Analytical (aggregation/particle diameter): SV-AUC
- Functional: SPR binding kinetics and potency (ELISA based)

Differently from example 2, the results from each test were obtained from the same analytical occasions. This means that the results of both samples were obtained e.g., in the same analytical run or sequence, and/or analyses on the same day, performed by the same technician.

Samples

The antibody used for this purpose was Omalizumab. This monoclonal antibody is a freeze-dried product manufactured at Halix (batch no. B3010640). The Omalizumab drug product was kept frozen (−20° C.) until further processing.

Sample 1 is the Omalizumab drug product as described above. This sample contains:
- Omalizumab (59%)
- L-histidine hydrochloride monohydrate (0.77%)
- L-histidine (0.49%)
- Sucrose (39.8%)
- Polysorbate (0.14%)

Sample 2 is the Omalizumab drug product after being exposed to the disclosure. This sample contains:
- Omalizumab (16%)
- Sucrose (10%)
- Chitosan (74%)
- PS20 (0.03%)
- Histidine (0.3%)

The particles of sample 2 were released in PBS buffer and frozen before shipment to external laboratories for characterization and comparison with sample 1.

A summary of the activities (functional, binding and analytical characteristics) conducted on the base material (for which sample 1 is representative) and the test material (for which sample 2 is representative) is provided in the next TABLE and FIGS. 17-21

Figure 17:
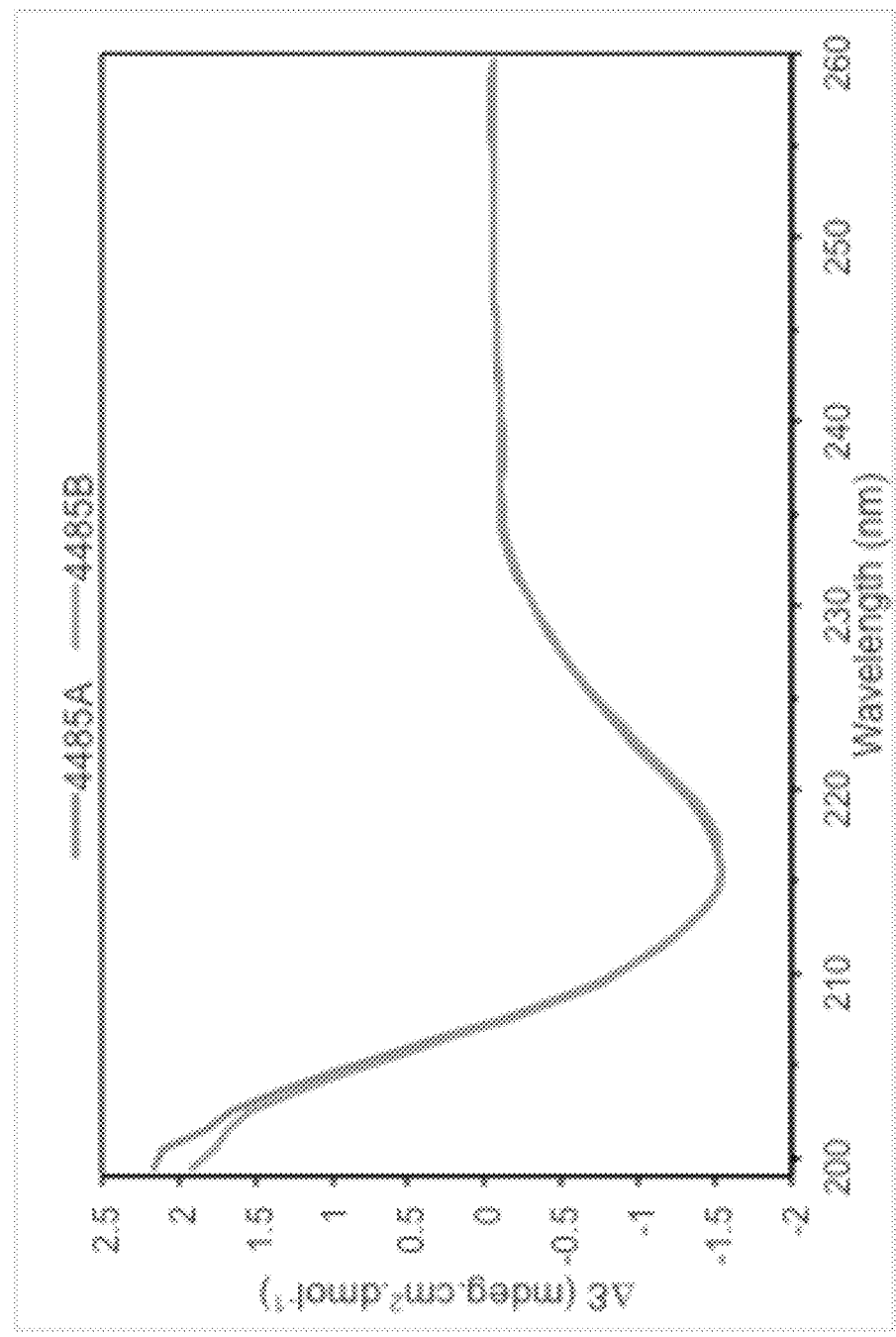
FIG. 17 Analysis of circular dichroism, Combined spectra of sample 1 (4485A) and sample 2 (4485B)
Figure 18:
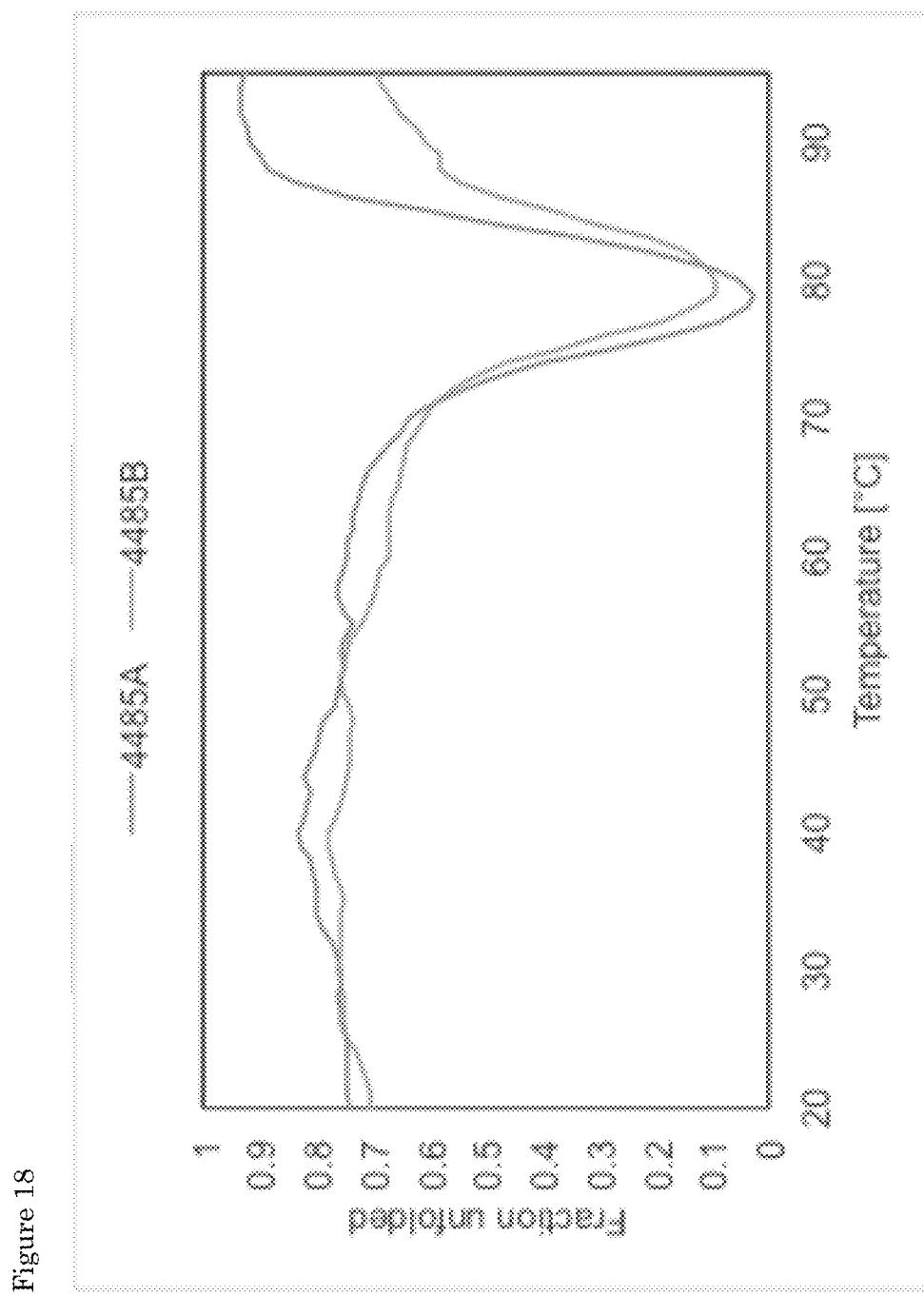
FIG. 18 Melt curve analysis. Combined spectra of sample 1 (4485A) and sample 2 (4485B).
Figure 19:
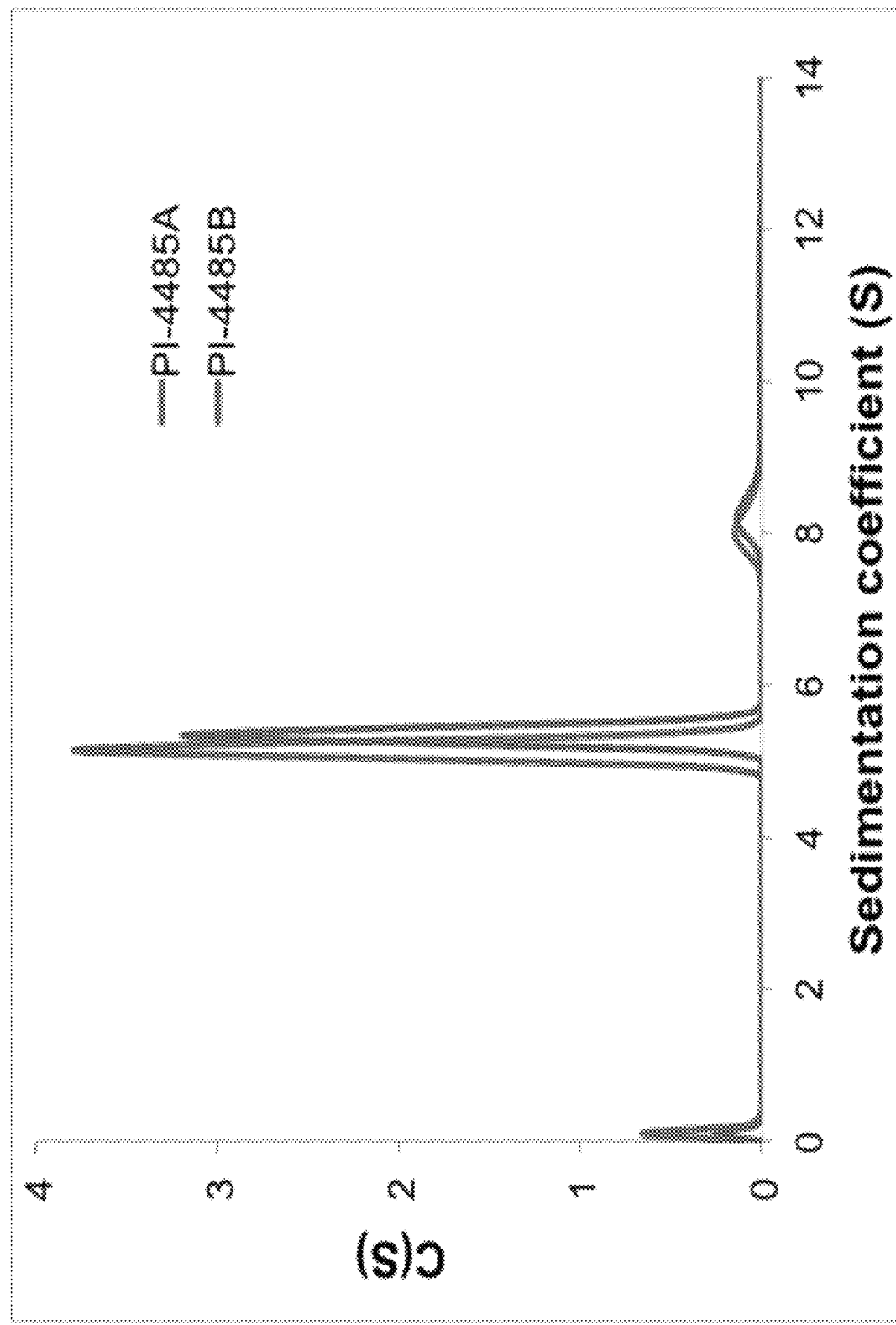
FIG. 19 Sedimentation velocity analysis. Overlay of the continuous sedimentation coefficient distribution of sample 1 (4485A) and sample 2 (4485B).
Figure 20:
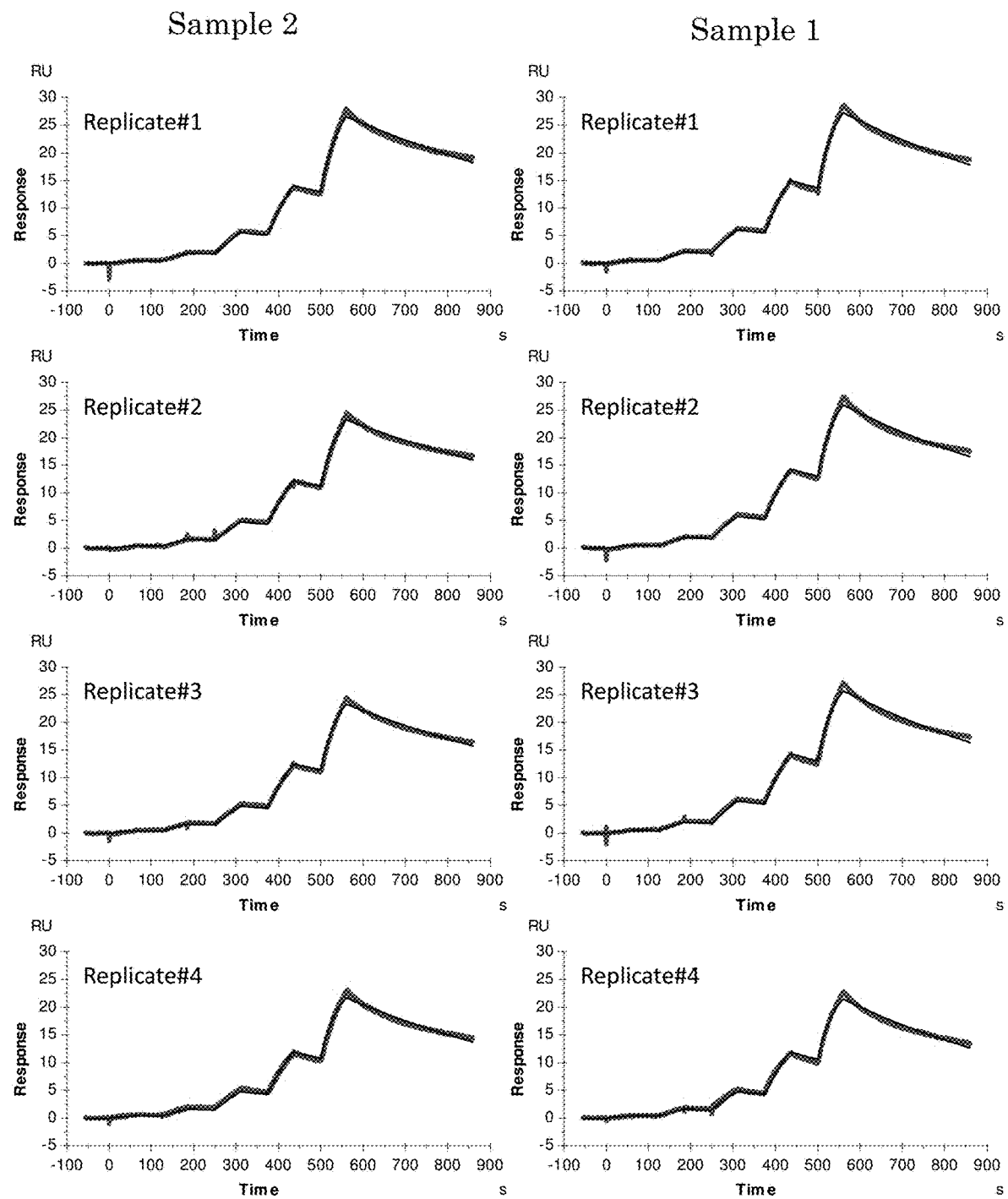
FIG. 20 Kinetic titration experiments measuring binding of sample 1 and sample 2 to immobilized human IgE, In each replicate, 4 (increasing) IgG concentrations were injected within a single cycle. Duplicate binding experiments are shown in each panel. Overlaid black lines represent a global fit of the data to a 1:1 interaction model.
Figure 21:
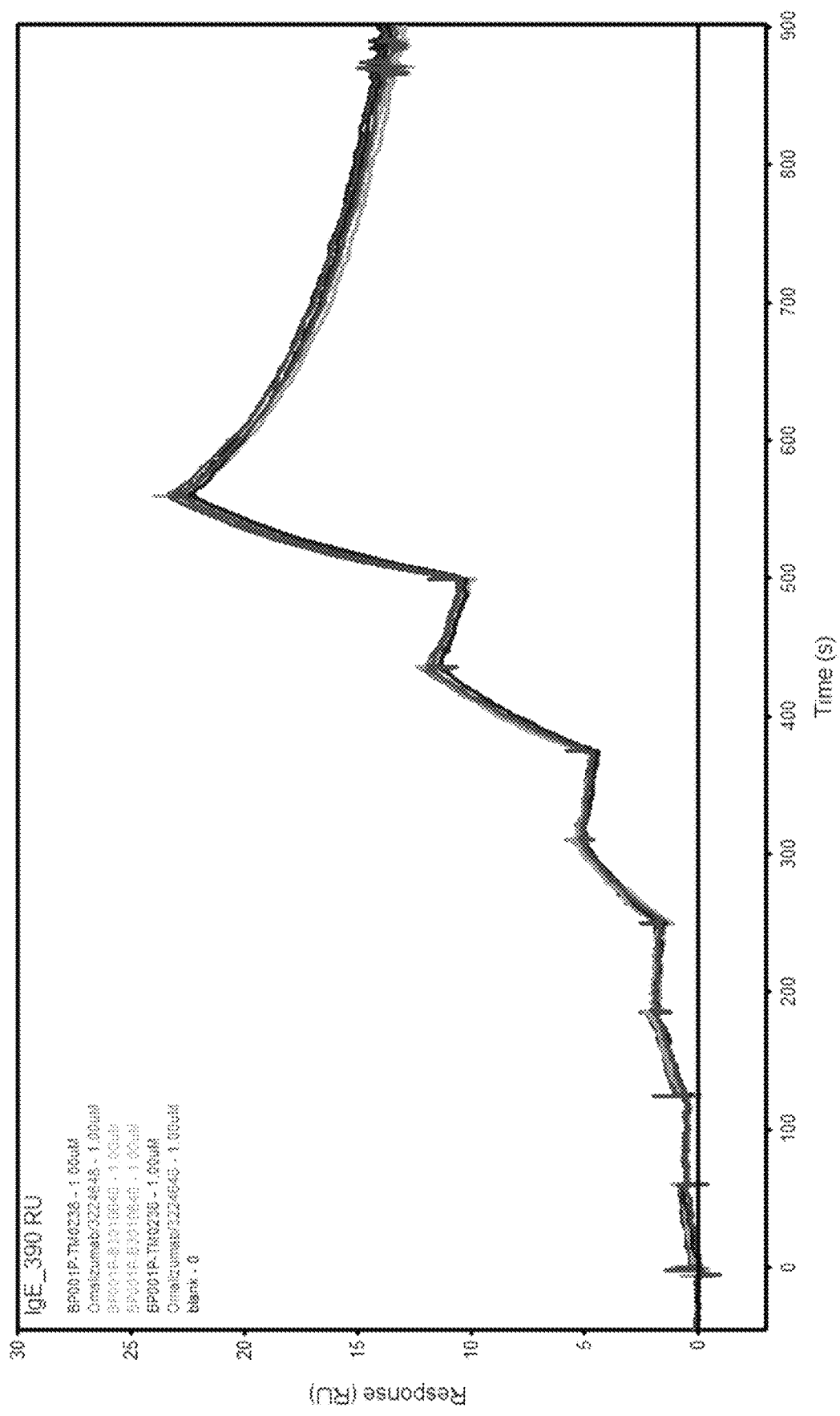
FIG. 21 Kinetic and affinity parameters derived from fitting the binding data of FIG. 20 to a 1:1 binding model. The lines represent sample 1 (orange), sample 2 (blue), and a XOLAIR® reference (red)

| Property | Lab | Method | Result | | | Reference |
|---|---|---|---|---|---|---|
| Structure analytics | PILL | Circular dichroism | Sample | α-helical (%) | Melting temperature (° C.) | FIGS. 17 and 18 |
| | | | Sample 1 | 0.0 ± 0.0 | 72.7 ± 1.2 | |
| | | | Sample 2 | 0.0 ± 0.0 | 74.7 ± 0.3 | |

Concentrations of the samples were set at 200 µg/mL in 10 mM potassium phosphate pH 7.6 and 100 mM potassium fluoride.
There was no α-helical secondary structure content in both of the samples tested and similar melt curves were produced from both samples.

-continued

| Property | Lab | Method | Result | Reference |
|---|---|---|---|---|
| | | | Conclusion: The overlapping Circular Dichroism spectral line shapes of the reference sample (sample 1 (4485A)) and the test sample (sample 2 (4485B)) indicates a high degree of secondary structural similarity across the molecules under the conditions applied. | |
| Intact mass | PILL | ESI-MS TOF | Intact mass was determined before and after deglycosylation, and in reduced and non-reduced form, using XOLAIR ® as reference. Glycosylated non-reduced mass determined was appr. 149,360 and 149,283, respectively, for PI-4485A and -B. Deglycosylated non-reduced mass determined was 146,350 and 146,351, respectively.<br>Treated:<br>Molecular mass of the light chain for both samples was 23,900 Da, which is in agreement with the theoretical mass (23,900 Da).<br>Molecular mass of the heavy chain for both samples was 49,255 and 49,258 Da, respectively, which is in agreement with the theoretical mass (49,384 Da). Molecular mass of appr. 50.7 kDa was observed for the heavy chain for all samples measured. For sample 2 however, other major species were observed.<br>Untreated:<br>The mass difference between the untreated and enzyme treated heavy chain was 1,446 and 1,443 Da, respectively. This mass difference corresponds to the major glycan that was observed during N-glycan analysis.<br>Overall conclusion: The intact masses for samples 1 and 2 were found to correspond to one another and to the theoretical mass of Omalizumab | |
| Aggregation | PILL | SV-AUC | | FIG. 19 |

| Sample | Weight average sedimentation coefficient (S) | Proportion of total signal (%) | Frictional ratio |
|---|---|---|---|
| Sample 1 | 5.2 | 81.5 | 1.5 |
| | 8.1 | 9.2 | |
| Sample 2 | 5.4 | 82.8 | 1.6 |
| | 8.3 | 9.8 | |

| Property | Lab | Method | Result | Reference |
|---|---|---|---|---|
| | | | Table: Approximate proportion of secondary structure content in all samples (%).<br>The continuous sedimentation coefficient distribution indicates the presence of a molecule in solution with a sedimentation coefficient at 5.3 S in both samples tested. There also appears to be a small proportion of a higher order species at 8.2 S for both samples of PI-4485. The proportion of sedimentation coefficient at 5.3 S was >80%. In contrast, the proportion for sedimentation coefficient 8.2 S was <10%. The difference in percentages is a result of accumulated background noise. The cause of the variation is not identifiable. The frictional ratio for the main peak was determined as ~1.5 indicating the molecule as somewhat elongated or asymmetric.<br>Conclusion: The sedimentation velocity data obtained from AUC showed that the PI-4485A and B were similar in their aggregation properties. | |
| Peptide mapping | PILL | LC-MS/MS | Sample 1: Analysis of the reference sample resulted in 93% coverage for the heavy chain and 100% sequence coverage for the light chain. The coverage for the heavy chain was reduced to 86% when a 95% data confidence filter was applied. N-terminal pyro-glutamination was evident by the detection of the heavy chain peptide 932.45 m/z (MH2)2+ in the trypsin digested sample. C-terminal truncation of lysine residue was evident in the heavy chain by the detection of the peptide 584.97 m/z (MH3)3+ in the Glu-C digested sample.<br>Sample 2: Analysis of the test sample resulted in 91% coverage for the heavy chain and 100% sequence coverage for the light chain. The coverage for the heavy chain was reduced to 83% when a 95% data confidence filter was applied. N-terminal pyro-glutamination was evident by the detection of the heavy chain peptide 932.44 m/z (MH2)2+ in the trypsin digested sample. C-terminal truncation of a lysine residue was evident by the detection of the peptide 876.90 m/z (MH2)2+ in the Glu-C digested sample.<br>Summary and conclusion:<br>Evidence of N-terminal pyro-glutamination was observed in the heavy chain of both the reference and test sample.<br>Evidence of C-terminal truncation of a lysine residue was observed in the heavy chain of both the reference and test sample.<br>Peptide mapping results were similar for both samples, with slight variation in the heavy chain | |
| Disulfide bridges | PILL | LC-tripleTOF MS | For both samples, the following postulated Cys bridges were confirmed: Cys22(H)-Cys96(H) Cys148(H)-Cys204(H) Cys265(H)-Cys325(H) Cys371(H)-Cys429(H) Cys23(L)-Cys87(L) Cys133(L)-Cys193(L).<br>The two postulated Cys bridges; Cys230(H)-Cys230(H), Cys233(H)-Cys233(H) in the hinge peptide were confirmed in both samples.<br>For both samples, the remaining interchain disulfide bridge Cys218(L)-Cys224(H) was not confirmed by mass spectrometry analysis, but could be inferred from the collective results in both samples.<br>Conclusion: there are no differences in disulfide bridges between sample 1 and 2 | |

| Property | Lab | Method | Result | Reference |
|---|---|---|---|---|
| Potency | VIP | | The relative potency value of sample 2 as compared to sample 1 tested was 82.9%, which is within the analytical error of the method applied. Conclusion: the potency of sample 1 and 2 is comparable. | |
| Binding kinetics | CSIRO (on behalf of VIP) | Surface Resonance Plasmon | Kinetic rate & affinity constants for IgG samples interacting with immobilized IgE (390 RU): | FIGS. 20 and 21 |

| IgG sample & batch number | $k_a \times 10^5$ ($M^{-1}s^{-1}$) | $k_d \times 10^4$ ($s^{-1}$) | $K_D$ (nM) | $R_{max}$ (RU) |
|---|---|---|---|---|
| Sample 2 | 7.1 ± 0.5 | 13.4 ± 1.3 | 1.9 ± 0.1 | 30 ± 3 |
| Sample 1 | 8.0 ± 0.1 | 15.4 ± 1.5 | 1.9 ± 0.2 | 31 ± 3 |

The Biacore T200 biosensor was used for comparative Surface Plasmon Resonance (SPR) analysis of binding interaction of the 2 different Omalizumab IgG samples against their target antigen (human IgE). IgG concentrations were injected sequentially within a single cycle from a low to high concentration (0.37 nM, 1.10 nM, 3.29 nM, 9.88 nM and 29.64 nM). The kinetic binding assay demonstrated no significant differences in the experimentally derived kinetic and affinity parameters of the two samples.

Conclusion

The data collected for sample 2 (untreated protein processed into particles and released in PBS) show great similarity with the data collected for sample 1 (untreated protein).

Analytical, structure and functional tests have shown that the molecule is intact and functional.

Example 4

Pharmacokinetics and Safety of Omalizumab in Minipig after Oral and Subcutaneous Administration Materials and Methods Materials used:

Avicel PH-101 Sigma Aldrich 11363
Fumed silica Sigma 55505
Eudragit L100-55 Evonik
Capsule Nr0 Spruyt Hillen 701
ELISA Shikari Q-OMA Matriks Biotek 30124471
Omalizumab Biosana Pharma BP001
Chitosan Sigma 448869
PS20 Sigma 428302
L-Histidine Sigma 1308505

Composition of the spray solution:

WFI containing 1% of a mixture composed of 10% sucrose, 73.7% chitosan, 0.03% PS20, 0.3% histidine, and 16% Omalizumab.

Preparation of Particulate Formulation

Particles were prepared by spraying of a solution containing coating material, Omalizumab and excipients into supercritical Carbon Dioxide.

Supercritical Spray Conditions:

Carbon dioxide ($CO_2$) 300 kh/h, nozzle 1650, solution 2.5 ml/min.

Obtained particle size distribution: $D_{10}$ 0.75 μm, $D_{50}$ 1.49 μm, $D_{90}$ 3.11 μm (Laser Diffraction Particle Size Analysis)

The mass load of Omalizumab in the particles was 16.4% by weight as determined by HPLC.

Preparation of Capsules for Oral (Po) Administration

Into each capsule (type 0), 156 mg particles (25 mg Omalizumab) was weighed. Each capsule was topped off with between 70 and 80 mg of an excipient mixture consisting of Avicell PH101 with 1% fumed silica.

The capsules were enteric-coated by dip coating into a solution containing Eudragit L100-55. Each capsule was dipped 5 times, which resulted in an average weight gain of about 38 mg per capsule. All of the capsules tested for the quality of the coating proved resistant to pH 2 Hydrochloric acid for two hours. The capsules dissolved in Phosphate Buffered Saline (pH 7.2) between 5 and 65 minutes.

Preparation of Solutions for Subcutaneous (Sc) Administration

Omalizumab solution was dissolved in water for injection (WFI) at a concentration of 50 mg/ml.

Animal Study

Eighteen male minipigs aged 4-6 years and weighing between 40 and 55 kg were dosed with 25; 50 or 75 mg Omalizumab by either lateral sc injection or po using a bolus shooter for capsules. For subcutaneous injection, Omalizumab solution dissolved in water for injection (WFI) was used. Oral administration was performed with particle-containing capsules. Blood was collected after 0 (pre-dose); 1; 3; 5; 24; 48; 120; 240; 480; 720 and 960 hours post administration from the jugular vein in standard Falcon tubes and K2-EDTA. Subsequently the blood was processed into serum by letting it clot for about 30 min-1 h. The serum was collected into Eppendorf tubes after centrifugation for 15 min at 3800 rpm. This was followed by centrifugation of the Eppendorf tubes for 2 min at 8000 rpm to remove residual red blood cells.

Serum samples were kept frozen (−20° C.) until further analysis of Omalizumab levels using an Enzyme Linked Immuno SorbentAssay (ELISA).

ELISA-Mediated Detection of Serum Levels of Omalizumab

Serum samples were assayed for levels of Omalizumab using a Shikari Q-Oma ELISA kit manufactured by Matriks Biotek. This kit is a sandwich principles, based on binding of Omalizumab present in the human plasma or sera to IgE on the bottom of the well. A horse radish peroxidase conjugate is subsequently added, which binds to the Omalizumab. After washing of the wells, the bound enzymatic activity is detected by addition of chromogen-substrate. The color developed is proportional to the amount of Omalizumab in the sample or standard.

Results were determined using the standard curve. The assay was investigated for the intended use of detecting Omalizumab in minipig serum instead of human serum.

Quantification (10-1000 ng/ml) was done using the calibration samples supplied with the kit. Serum samples were diluted 10 times prior to incubation.

Safety Parameters

Blood and serum samples for hematology and chemistry assessment were taken at baseline t=0 and 24, 48, 120, 240, 480, 720 and 960 hours after dosing.

The following hematology parameters were measured: White Blood Cell Count, Red Blood Cell Count, Hemoglobin, Hematocrit, Mean Cell Volume, Mean Cell Hemoglobin, Mean Cell Hemoglobin Concentration, Platelet Count, Reticulocyte Count, Reticulocyte Count, Red Blood Cell Distribution Width, Neutrophils, Lymphocytes, Monocytes, Eosinophils, Basophils, Large Unstained Cells.

For serum chemistry, it was determined: Sodium, Potassium, Chloride, Total Protein from protein gel, Alkaline Phosphatase, Cholesterol, Phosphorus, Aspartate Amino-transferase, Alanine Amino-transferase, Albumin, Albumin/Globulin ratio, Blood Urea Nitrogen, Glucose, Gamma glutamyl trans-peptidase, Calcium, Creatinine.

Results

Animal Welfare and Safety:

No animals showed abnormal behavior or signs of pain or other adverse effects.

Animals were weighed two weeks before commence of the study and one week after dosing. No significant trend in either increase or decrease of body weight was observed, a positive corroboration of the animal their health during the study.

Serum Levels of Omalizumab

Figure 22:
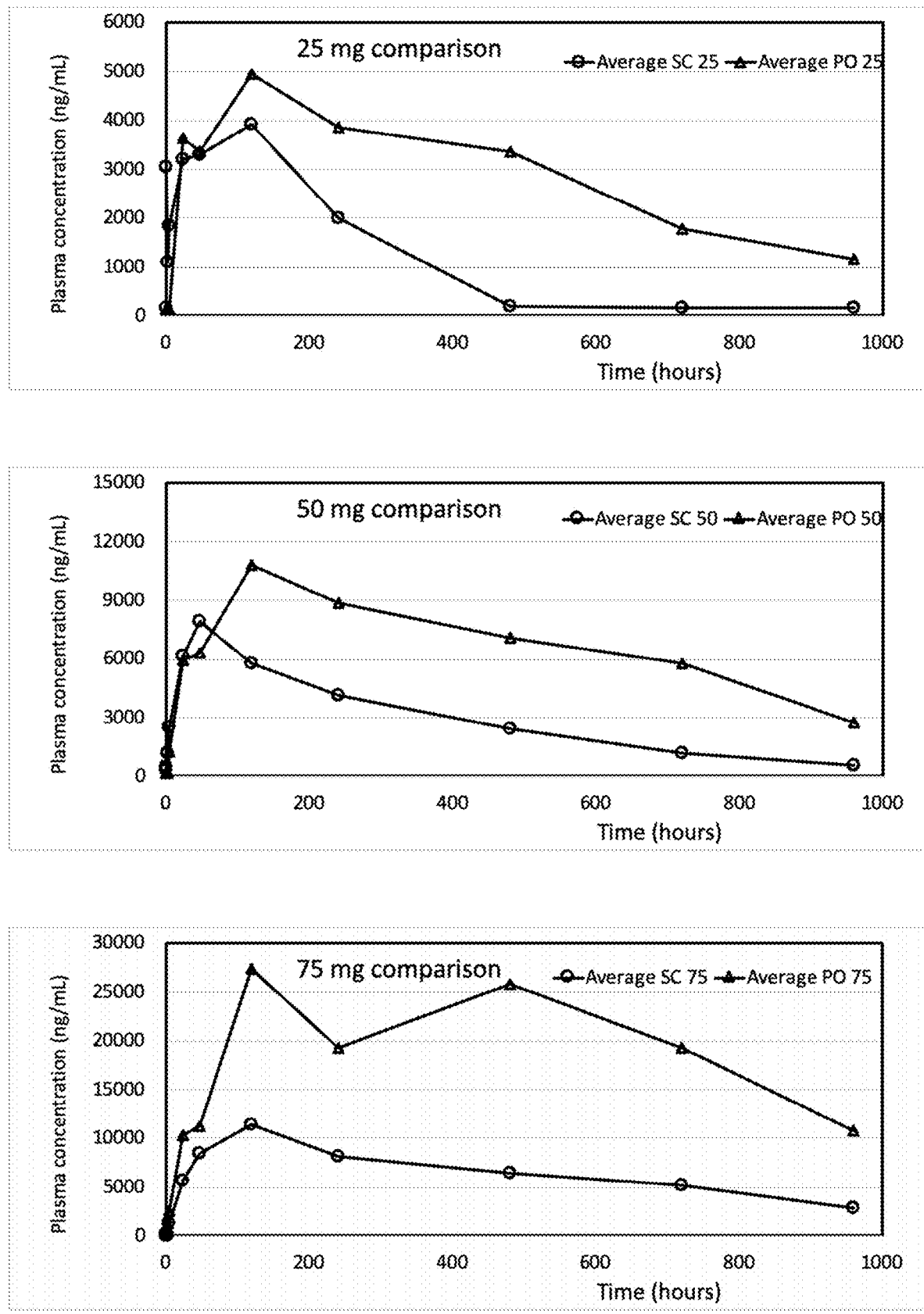
FIG. 22 Serum levels of Omalizumab in minipigs after oral and subcutaneous dosing

All types of dosing show an initial, dose-dependent, rise of Omalizumab in serum and a gradual washout over time (see FIG. 22).

Oral administration indicates a higher bioavailability when compared to the subcutaneous administration. Upon subcutaneous injection, maximum serum levels of 12000; 8000 or 4000 ng/ml were reached when dosing 25, 50 or 75 mg Omalizumab, respectively. Oral administration resulted in maximum serum levels of 27000, 11000 or 5000 ng/ml when dosing 25, 50 or 75 mg Omalizumab, respectively.

The T½ values of the oral dosing are longer compared to subcutaneous injection. The relative bioavailability of the oral dosing was a factor 2.3-3.1 compared to subcutaneous injection.

The Tmax values (i.e., the time it takes to reach the maximum concentration) is clearly prolonged for all the oral dosing groups, when compared to the subcutaneous group.

Safety:

No significant changes were seen in all parameters, when compared to the pre-dose values.

Conclusions:

This study shows that oral dosing of Omalizumab, using stomach-resistant capsules filled with Omalizumab formulated into microparticles, results in an excellent dose-dependent high bioavailability in serum of minipigs. The particle formulation proved capable of transporting Omalizumab across the intestine epithelium into the blood stream, without toxic effects as measured in a range of parameters in blood and serum.

It is evident that when using the microparticle formulated oral dosing of Omalizumab, this may result in a higher bioavailability in human when compared to the usual clinical subcutaneous dosing route of Omalizumab.

The biostatistics of the sc group shows similarities with results derived from literature based on sc dosing in a clinical setting (Rivière at al., J. Bioequiv. Availab 2011, 3; 6), with respect to Tmax (96 vs 120 hr) and T. (385 vs 580 hr).

The invention claimed is:

1. A method for preparing a pharmaceutical composition capable of oral delivery of a systemically active ingredient to a subject, the method comprising:
    preparing an aqueous composition comprising:
        a protein with a mass of at least 10 kiloDaltons, a nucleic acid molecule of at least 15 nucleotides, or a combination thereof, as a systemically active ingredient in an amount of 0.02-25% of the dry weight of the composition,
        monosaccharide or disaccharide in an amount of 2-25% of the dry weight of the composition,
        a pharmaceutical excipient in an amount of 0-10% of the dry weight of the composition, and
        chitosan in an amount of at least 48.3% of the dry weight of the composition;
    spraying the prepared aqueous composition into an anti-solvent and/or supercritical fluid in which a water fraction of the aqueous composition is soluble or miscible and in which the solutes of the aqueous composition are not soluble, thereby precipitating the solutes and producing particles with an average diameter of 50 nanometers (nm) to 20 micrometers (μm);
    collecting the particles; and
    preparing the pharmaceutical composition capable of oral delivery comprising the particles that comprise the systemically active ingredient;
    wherein the chitosan was first dissolved in acidified water.

2. The method according to claim 1, wherein an anti-solvent is utilized, which anti-solvent is supercritical $CO_2$.

3. The method according to claim 2, wherein the supercritical CO2 has a temperature of 30-55 degrees Celsius and/or a pressure of at least 73 Bar.

4. The method according to claim 1, wherein the prepared aqueous composition comprises an amino acid in an amount of 0.001-0.5% by dry weight of the final aqueous composition.

5. The method according to claim 1, wherein the prepared aqueous composition comprises one or more of a permeation enhancer, a solubilizer, an emulsifier, and a combination thereof.

6. The method according to claim 1, wherein the prepared aqueous composition comprises polysorbate 20 to 80 and/or sorbitan stearate.

7. The method according to claim 1, wherein the systemically active ingredient comprises an oligonucleotide, a cytokine, an enzyme, a soluble protein ligand to a cellular receptor, a factor of the blood clotting system, a fusion protein, and/or an antibody.

8. The method according to claim 1, wherein the systemically active ingredient comprises an interferon, an erythropoietin, an antibody, a Factor VIII, a Factor IX, a Von Willebrand factor, a tumor necrosis factor ("TNF"), a growth hormone ("GH"), etanercept, or a prolidase.

9. A collection of particles with an average diameter of 50 nm to 20 μm obtained by the method according to claim 1.

10. A collection of particles with an average diameter of 50 nm to 20 μm obtainable by the method according to claim 1, wherein the collection of particles comprises a homogeneous distribution of:
    a protein with a mass of at least 10 kiloDaltons, a nucleic acid molecule of at least 15 nucleotides, or a combination thereof, as an active ingredient in an amount of 0.02-25% of the dry weight of the particles;
    monosaccharide or disaccharide in an amount of 2-25% of the dry weight of the particles;
    a pharmaceutical excipient in an amount of 0-10% of the dry weight of the particles; and chitosan in an amount of at least 48.3% of the dry weight of the particles.

11. The collection of particles of claim 9, wherein the systemically active ingredient thereof comprises an antibody.

12. The collection of particles of claim 11, wherein the collection of particles comprises:
   5-25% omalizumab of the dry weight of the particles;
   2.5-20% sucrose of the dry weight of the particles;
   0.025-0.2% polysorbate 20-80 of the dry weight of the particles;
   2.5-10% amino acids of the dry weight of the particles; and
   at least 44.8% chitosan of the dry weight of the particles.

13. The collection of particles of claim 11, wherein the antibody comprises omalizumab.

14. The collection of particles of claim 10, wherein the active ingredient comprises omalizumab.

15. The method according to claim 1, further comprising:
   orally administering the pharmaceutical composition to a subject in need thereof so as to deliver a protein of at least 10 kDa, or a nucleic acid molecule of at least 15 nucleotides to the subject as an active ingredient in a therapeutically relevant amount.

16. A method of treating a subject in need thereof, the method comprising:
   administering a pharmaceutical formulation in oral dosage form, wherein the pharmaceutical formulation comprises the collection of particles of claim 9.

17. The method according to claim 16, wherein the dosage form is a tablet, a hard capsule, a soft capsule, a caplet, a lozenge, a pill, a mini-tablet, a pellet, or a powder.

18. A method of treating a subject in need thereof, the method comprising:
   administering a pharmaceutical formulation in oral dosage form, wherein the pharmaceutical formulation comprises the collection of particles of claim 10.

19. The method according to claim 18, wherein the dosage form is a tablet, a hard capsule, a soft capsule, a caplet, a lozenge, a pill, a mini-tablet, a pellet, or a powder.

* * * * *